US 6,655,015 B2

(12) United States Patent
Kraenzle

(10) Patent No.: US 6,655,015 B2
(45) Date of Patent: Dec. 2, 2003

(54) DPA AUTOMATED ASSEMBLY AND PACKAGING MACHINE

(76) Inventor: David G. Kraenzle, 12845 Big Bend, St. Louis, MO (US) 63122

(*) Notice: Subject to any disclaimer, the term of this patent is extended or adjusted under 35 U.S.C. 154(b) by 0 days.

(21) Appl. No.: 09/821,880

(22) Filed: Mar. 30, 2001

(65) Prior Publication Data

US 2002/0139091 A1 Oct. 3, 2002

(51) Int. Cl.[7] .............................. B65B 5/08; B65B 5/10; B65B 5/12; B65B 7/00; B23Q 1/26
(52) U.S. Cl. .............................. 29/783; 53/237; 53/247; 29/783; 29/791
(58) Field of Search .................... 53/467, 53, 52, 53/237, 247; 433/125; 29/430, 783, 784, 787, 791, 792, 793, 795, 799, 896.1

(56) References Cited

U.S. PATENT DOCUMENTS

| | | | | |
|---|---|---|---|---|
| 4,445,611 A | * | 5/1984 | Shofu | 206/369 |
| 4,685,277 A | * | 8/1987 | Ilsemann | 53/474 |
| 4,759,713 A | * | 7/1988 | Heiss et al. | 433/141 |
| 4,884,330 A | * | 12/1989 | Sticht | 29/430 |
| 4,894,908 A | * | 1/1990 | Haba et al. | 29/711 |
| 4,971,189 A | * | 11/1990 | Fleming et al. | 198/346.1 |
| 5,052,540 A | * | 10/1991 | Matsuyama et al. | 198/346.1 |
| 5,120,220 A | * | 6/1992 | Butler | 433/125 |
| 5,165,218 A | * | 11/1992 | Callahan, Jr. | 53/243 |
| 5,237,801 A | * | 8/1993 | Hillam et al. | 53/142 |
| 5,247,733 A | * | 9/1993 | Kubota et al. | 29/785 |
| 5,339,607 A | * | 8/1994 | Regier | 53/240 |
| RE34,997 E | | 7/1995 | Kraenzle | 433/126 |
| 5,533,608 A | * | 7/1996 | Adams et al. | 198/478.1 |
| 5,622,025 A | * | 4/1997 | Kitagawa et al. | 198/403 |
| 5,683,247 A | * | 11/1997 | Bailey | 433/104 |
| 5,852,869 A | * | 12/1998 | Gieskes et al. | 29/740 |
| 6,249,969 B1 | * | 6/2001 | Komatsu et al. | 29/791 |
| 6,357,102 B1 | * | 3/2002 | Benner | 29/430 |

* cited by examiner

Primary Examiner—Rinaldi I. Rada
Assistant Examiner—Gloria Weeks
(74) Attorney, Agent, or Firm—Harness, Dickey & Pierce, P.L.C.

(57) ABSTRACT

This patent relates to a machine that automatically assembles, inspects, and packages disposable prophylaxis angles. The machine includes a movable table including a plurality of fixtures on which angle components are assembled and the assembled angles are inspected. The movable table is surrounded by a number of stations, each of which performs a different operation of the assembly and inspection procedure. Feeders automatically supply the angle components to their respective stations for assembly. Angles that are incorrectly assembled are automatically rejected. Properly assembled angles are automatically sealed in individual bags. Individually bagged angles are counted into batches by the machine and automatically sealed into cartons.

5 Claims, 33 Drawing Sheets

DPA AUTOMATED ASSEMBLY AND PACKAGING MACHINE

FIELD OF THE INVENTION

This invention generally relates to a machine that automatically assembles, inspects, and packages dental products and, more specifically, disposable prophylaxis angles.

BACKGROUND OF THE INVENTION

Dentists and hygienists have used prophylaxis (prophy) angles for over 100 years to clean and polish teeth. Until recently, prophy angles were made of metal so they could be used over and over again, one patient after the next. To prevent the spread of infectious diseases from patient to patient, the dentist or hygienist cleaned and sterilized the angle after each use.

In recent years, a market has developed for disposable prophy angles due in part to increased awareness and concern for the spread of infectious diseases such as hepatitis and AIDS. Because disposable prophy angles are discarded after each use, they must be produced in extraordinarily greater quantities than the metal angles they have replaced. As a result, a need exists to develop cost-effective processes for manufacturing disposable prophy angles in large quantities.

There are three basic steps in the production of disposable prophy angles: the manufacture of the components of the angle, the assembly of the angle components, and the packaging of the assembled angles. The packaging step can be further subdivided into individual bagging, batch counting, and carton sealing.

The manufacture of individual angle components is already highly mass produced through means such as injection and compression molding, the prior means being the dominant method. The assembly step, however, is done largely by hand since automated machinery for prophy angle assembly is not available. Such equipment must be designed specifically for this. The batch-counting step is also performed largely by hand since this equipment must also be designed specifically for this purpose and because, to be practical, it must be integrated with other automated machinery. Carton sealing equipment, although readily available, must also be integrated with other automated machinery in order to be practical.

While the assembly of prophy angles by hand has the advantage of requiring minimal initial investment; it has several inherent major disadvantages. Lubrication on the bearings and gears of disposable prophy angles provides smoother operation and increased life. Yet, when done by hand, this step can be somewhat difficult and add a significant amount of time, and therefore cost, to the assembly operation. Controlling the amount of lubricant applied in hand assembly can also be difficult. An angle that is under-lubricated may run less smoothly or overheat when used. Lubricant may leak out of an over-lubricated angle making it messy for the end user, and ultimately the patient in whose mouth the device will be used.

Another disadvantage is the variability in quality of the finished product. Due to the repetitious nature of assembly by hand, it is often difficult for assembly personnel to remain focused on their work. For this reason, along with the fact that large numbers of assembly personnel are required, variability in the quality of the finished product, especially related to the application of lubricant, is a constant problem.

All of the disadvantages above add to the cost of hand-assembled disposable prophy angles in order to ensure that they are clean, safe, and high quality.

SUMMARY OF THE INVENTION

The present invention is directed to a machine and method for assembling a dental product. The dental product generally includes a body, first and second gears, and a tool. The machine comprises feeders for automatically supplying the component parts and contiguous assembly stations coupled to the feeders for receiving the component parts and for performing assembly steps of the dental product. The assembly stations comprise a body station for receiving and holding the body of the product, at least two gear stations for introducing the first and second gears of the dental product into the body, and a tool station for connecting the tool to the second gear of the dental product. In a preferred embodiment, the machine further comprises a lubricating station for applying lubricant to the gears of the dental product.

In other preferred aspects of the invention, automated bagging and packaging equipment is provided. For this aspect of the invention, the machine comprises a first conveyor for automatically moving assembled angles to a bagging unit. The bagging unit automatically bags the assembled angles. The machine also preferably includes a batch-counting unit for automatically counting a batch of assembled and bagged dental products and placing the batch in a container.

A second conveyor is provided for moving assembled and bagged dental products from the bagging unit to the batch-counting unit. The machine preferably includes a batch conveyor system comprising a first accumulating conveyor for supplying containers to the batch-counting unit and a second accumulating conveyor for moving a container with the batch to an unloading station. The machine can also include a carton-sealing unit for sealing the container. The carton-sealing unit is preferably located on the second accumulating conveyor, prior to the unloading station.

A method of assembling a dental device with automated machinery is also disclosed herein. The dental device has a body and at least two gears. The body has a first end adapted to receive a drive mechanism for turning the gears of the dental device and a second end for holding a dental tool. The second end has a closure for closing off the second end of the dental product. The method for automatically closing the body of the dental device after the gears have been introduced into the body comprises the steps of receiving the body of the angle with gears loaded into the body. The body is located on a mounting post that engages the first end of the dental device to hold it. The method also comprises closing the body of the dental device by using a mechanism that snaps the closure to a closed position to close off the second end of the angle. In a preferred aspect of the invention, the method specifically comprises closing the dental device by engaging an outer surface of the closure and rotating it to the closed position.

In another aspect of the invention, the method of assembling the dental product comprises the steps of transferring the body of the dental device from a body feeder to a moveable table and advancing the table to move the body to a first gear loading station and loading the first gear into the body. The method further comprises advancing the table to move the body to a second gear loading station and loading the second gear into the body and advancing the table to move the body to a closure station and closing the body of the dental device. Finally, the method comprises advancing the table to move the body to a tool loading station and connecting the tool to the second gear of the dental device. Also in the preferred embodiment, the first and second gears are lubricated.

The method can also include the step of advancing the table to move the body to an inspection station, and inspecting the angle to determine whether it has been assembled properly. Dental devices that have not been assembled properly are preferably diverted to a rejection container and dental devices that have been assembled properly are diverted to a conveyor to convey the properly assembled angles to a bagging station. At the bagging station, the assembled angles are bagged. It is also preferable to convey the bagged dental devices to a batch-counting device and count the bagged dental devices using the batch-counting device. After a pre-selected number of angles are counted, a batch of dental devices is created. The batch is loaded into a container and conveyed to an unloading station. The invention also preferably includes the step of sealing the container prior to conveying the container to the unloading station.

It can therefore be seen that the present invention overcomes the problems associated with the prior art. The machine and method for mass assembling dental tools provides for rapid and consistent quality production of the dental tools. Problems with worker inattention and deviations in quality control are overcome by the present invention. Moreover, the cost to assemble and package the dental devices is significantly reduced. These and more specific aspects of the invention are described more fully below.

DESCRIPTION OF THE PREFERRED EMBODIMENT

Figure 1:
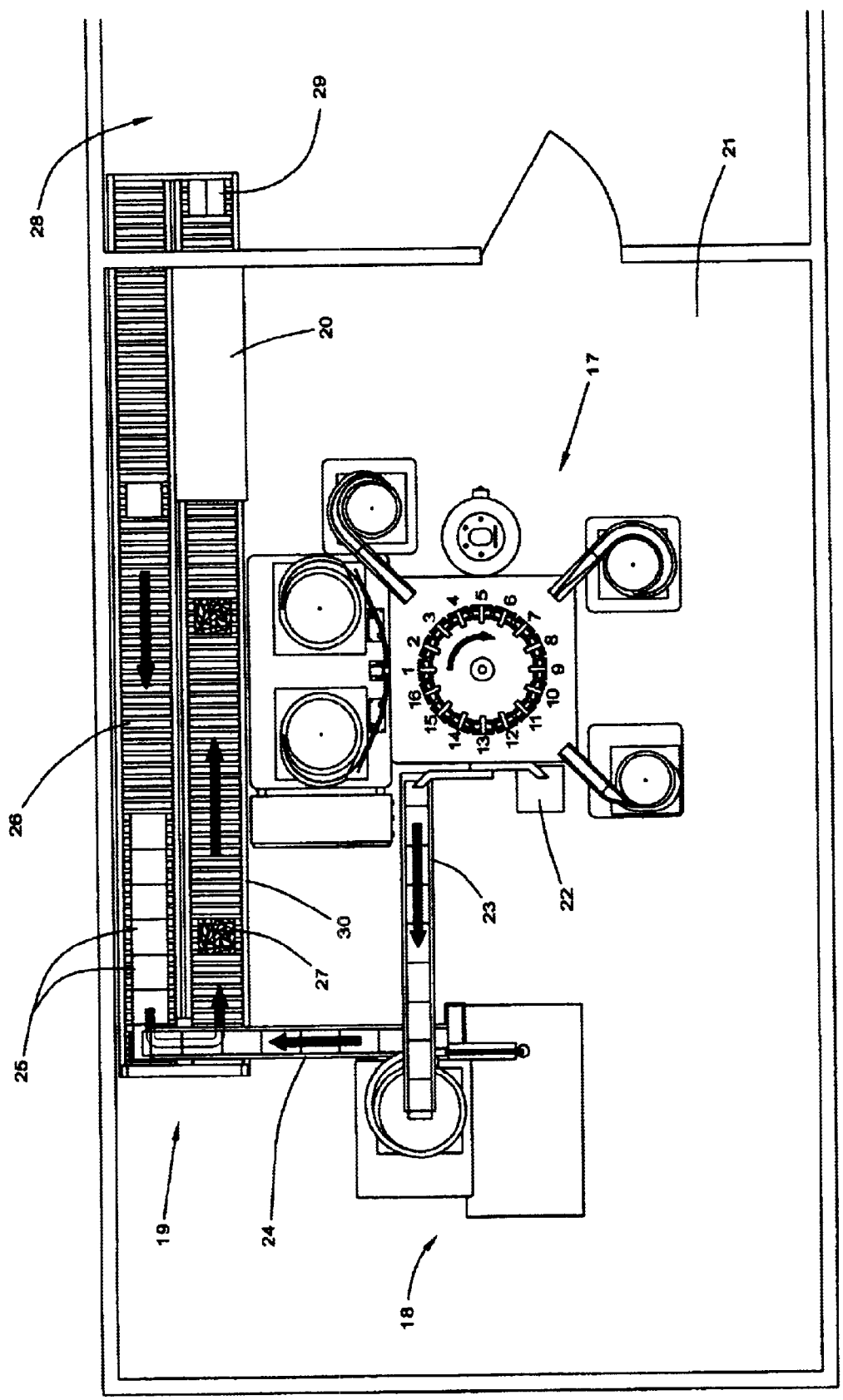
FIG. 1 is a plan view of the machine.

Referring to FIG. 1, the preferred embodiment of the present invention comprises an assembly unit 17, a bagging unit 18, a batch-counting unit 19, and a carton-sealing unit 20. The preferred arrangement of these units relative to one another is shown in FIG. 1. They may, however, be arranged in any convenient manner as space permits.

In FIG. 1, the assembly unit 17 assembles the components of the prophy angle, and inspects the assembled angles. Upon inspection, the angles are either accepted or rejected. The rejected angles are collected in a container 22 for later review.

A first belt conveyor 23 carries the accepted angles to the bagging unit 18, which individually bags each angle. A second belt conveyor 24 carries the bagged angles to the batch-counting unit 19 where batches of angles are counted and placed into empty cartons 25.

A first accumulating conveyor 26 supplies empty cartons 25 to the batch-counting unit 19. A second accumulating conveyor 30 carries the full cartons 27 from the batch-counting unit 19 through the carton-sealing unit 20 to a location 28 where the sealed cartons 29 can be handled by personnel for shipment.

Figure 2:
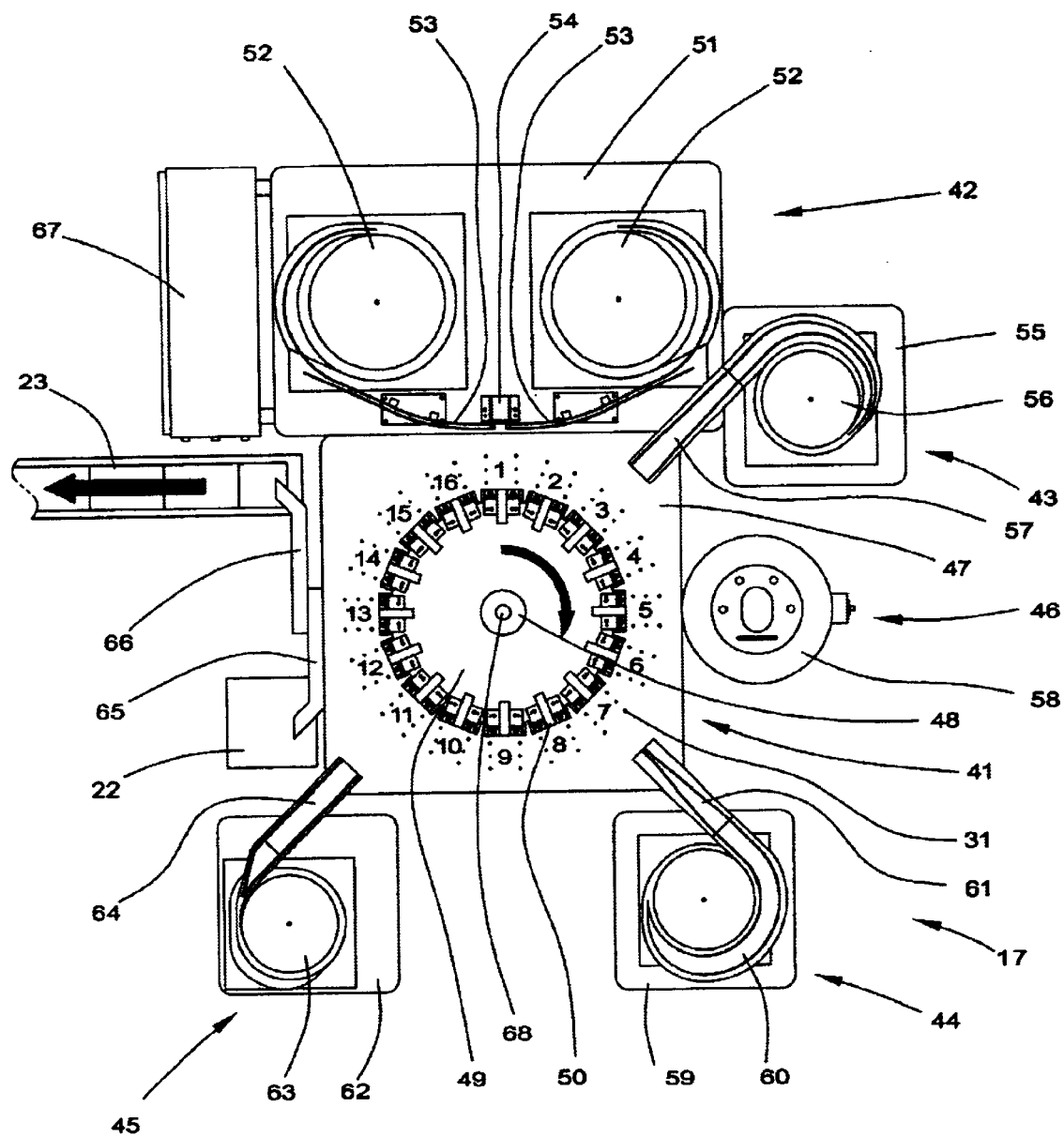
FIG. 2 is an enlarged plan view of the assembly unit of the machine illustrated in FIG. 1.

The assembly unit 17, shown in FIG. 2, consists of a center main module 41 attached to four surrounding feed modules 42 thru 45 and a lubricant-dispensing module 46. Four feed modules are preferred because this embodiment is intended to assemble the disposable prophy angle described in U.S. Pat. RE34,997. Since the number of feed modules is equal to the number of angle components to be assembled, alternate embodiments may include more or less than four feed modules. The invention disclosed herein can be readily modified to accommodate the design of other dental products, including disposable prophy angles, as understood by those skilled in the art.

The main module 31 consists of a base 47 (shown in FIGS. 10, 11, 13, 17–21, 25–27, 29–30, 32–34, and 38), an indexer 48, a dial plate 49, fixtures 50 an station 1 thru 16. Note in FIGS. 1 and 2 that the machine components mounted at each station 1 thru 16 are not shown. These components have been omitted for clarity. FIGS. 7 thru 39 are drawings of the stations 1 thru 16 presented individually so that each may be illustrated with the necessary detail.

Each station 1 thru 16 performs a different operation of the assembly or inspection procedure. Sixteen stations are preferred in this embodiment. Thirteen of these stations are provided to complete the necessary assembly and inspection operations, and three stations are provided for additional operations if the need arises. In alternate embodiments, more or less than sixteen stations may be used depending on the number of operations required for the particular disposable prophy angle to be assembled and inspected.

The main module base 47 is preferably a table-like welded steel frame approximately thirty inches in height with a welded and ground steel top that provides a precision machined surface for mounting the indexer 48 and stations 1 thru 16. The base 47 is sized to accommodate the indexer 48, dial plate 49, fixtures 50, and stations 1 thru 16.

An indexer 48 is mounted in the center of the main base 47. As is common in the art, the indexer 48 has the same number of positions as the number of stations surrounding it so that each position on the dial plate 49 corresponds to a station 1 thru 16. In the preferred embodiment, the prophy angle described by U.S. Pat. RE34,997 is to be assembled. A sixteen-position indexer is preferred in this embodiment because sixteen position indexers are common purchased items to those skilled in the art and because sixteen positions will accommodate all of the operations required in this embodiment with a few stations remaining open for additional operations or to allow the machine to be adapted to assemble a prophy angle other than the angle described in U.S. Pat. RE34,997.

The indexer 48 preferably includes a stationary center post 68, a feature common to commercial indexers. This stationary center post 68 is mounted to the main base 47 through a hole in the center of the indexer 48 and the dial plate 49. The center post 68 is preferably made from tubular steel such as pipe or mechanical tubing to provide a stationary support in the center of the dial plate 49 and to serve as a conduit for electrical wiring and/or compressed air lines. The specific use of the center post 68 will be discussed later.

The circular dial plate 49 is mounted to the indexer 48 such that together, the indexer 48 and the dial plate 49 form a movable table with sixteen precise positions. Sixteen fixtures 50 (one for each position of the indexer) are mounted to the dial plate 49, equally spaced along the perimeter. Each fixture 50 is used to hold the prophy angle components as they are assembled. Each fixture 50 is identical and, therefore, interchangeable with any other.

In a circle around the dial plate 49, sixteen stations 1 thru 16 are paired in a one-to-one relationship with the sixteen fixtures 50 on the dial plate 49. At each station 1 thru 16, a hole pattern 31 is provided in the main base that is common to all of the stations 1 thru 16. This common hole pattern 31 is part of a modular design which simplifies construction and reduces cost by allowing stations 1 thru 16 to be constructed using interchangeable components. The modular station design also increases versatility and reduces maintenance time by allowing stations to be quickly interchanged and/or replaced.

Each fixture 50, shown in detail in FIGS. 3 thru 6, consists of a base plate 77 to which two mounting posts 78 are attached by a nut 79. A mounting post 78 serves the purpose of securely supporting the angle components during assembly. The mounting post 78 resembles the Doriot nose of the dental handpiece and, like the Doriot dental handpiece, is sized to snugly receive a prophy angle. This method of securing the angle is preferred since the dimensions of the Doriot nose and the mating features of dental angles have been standardized by the International Standards Organization (ISO). Therefore, aesthetic differences or changes in the design of the angle have no effect on the ability of this machine to assemble the angle. Angles of different shapes and sizes can be assembled without requiring retooling.

A key 80 extends perpendicularly from the mounting post 78. This key 80 serves to maintain proper alignment of the angle on the post 78 by engaging the Doriot slot in the body of the angle to prevent the angle from rotating. The key 80 is preferably formed from a pin press fit into a hole in the side of the mounting post.

Figure 5:
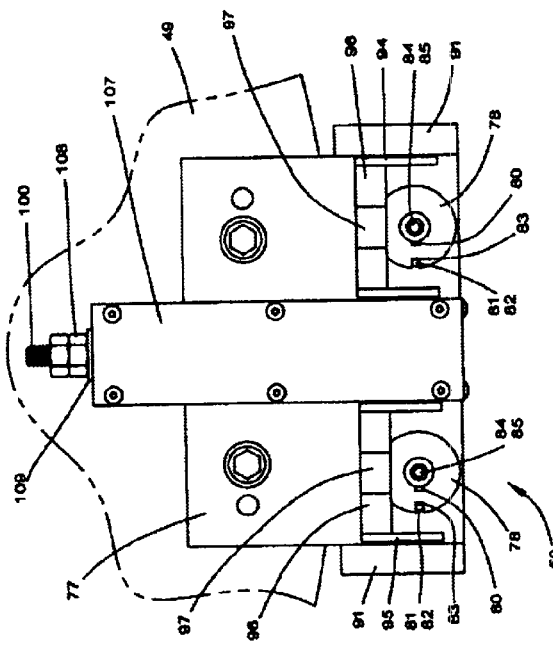
FIG. 5 is a plan view of a fixture mounted to the dial plate illustrated in FIGS. 1 and 2.
Figure 6:
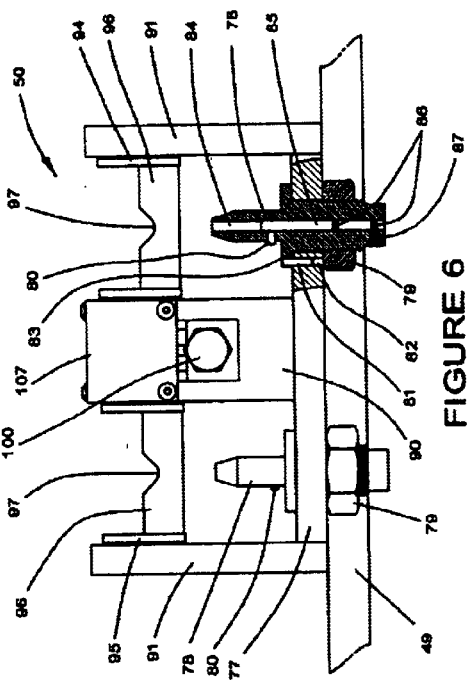
FIG. 6 is a front view of a fixture mounted to the dial plate illustrated in FIGS. 1 and 2.
Figure 3:
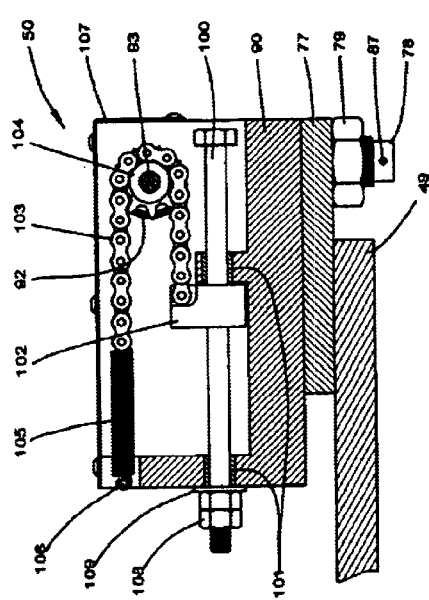
FIG. 3 is a cross-sectional side view of a fixture mounted to the dial plate illustrated in FIGS. 1 and 2.
Figure 4:
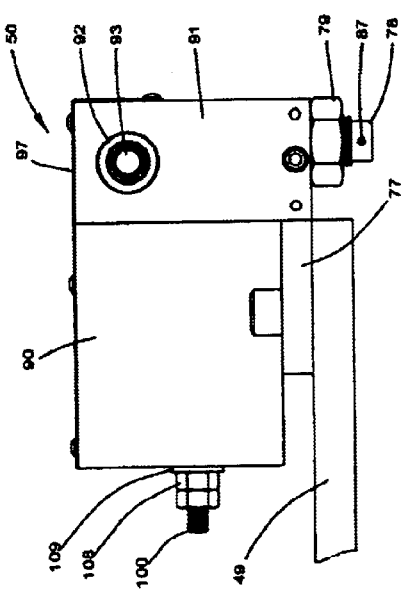
FIG. 4 is a side view of a fixture mounted to the dial plate illustrated in FIGS. 1 and 2.
Figure 7:
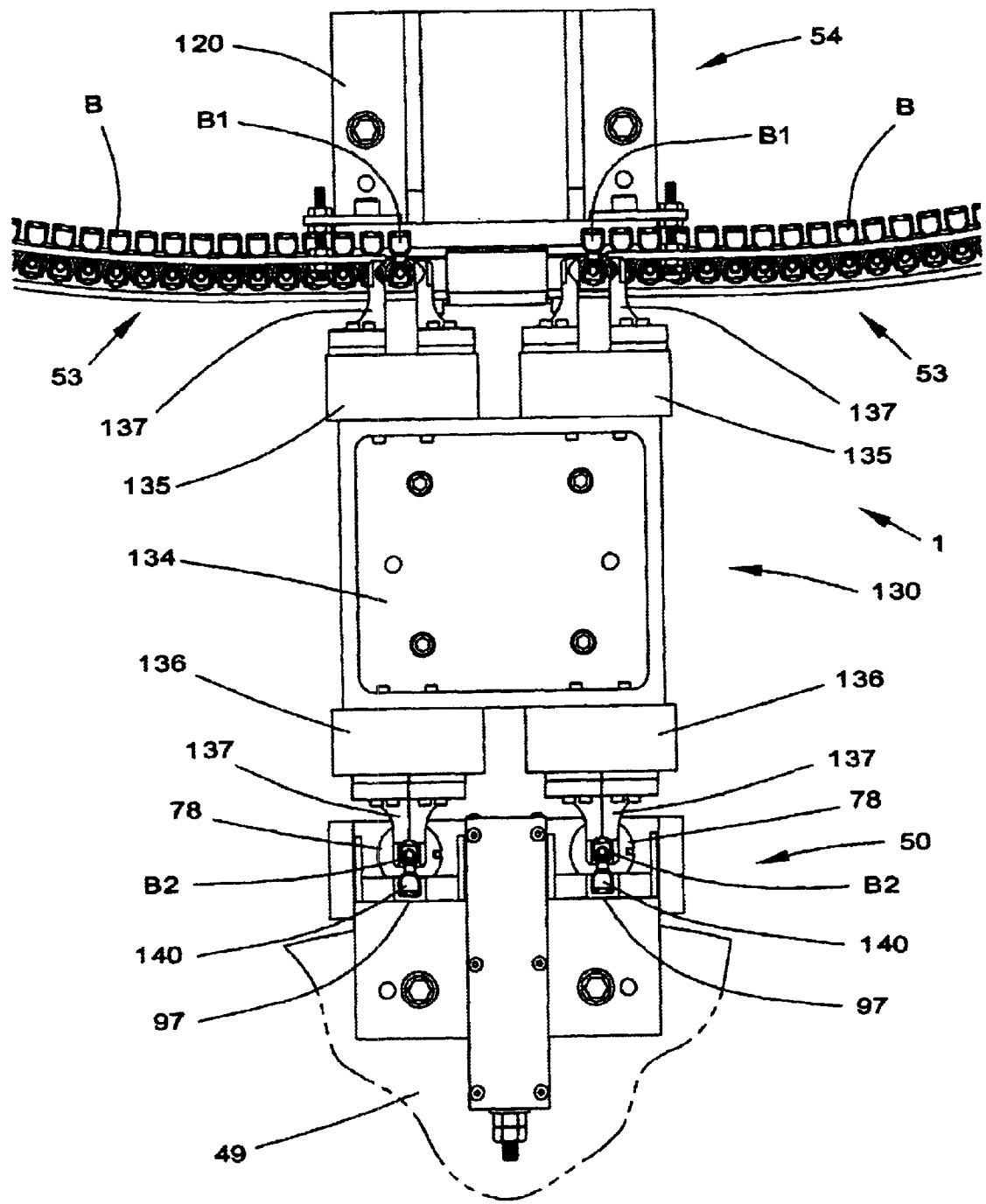
FIG. 7 is a plan view of Station One of the preferred embodiment.
Figure 9:
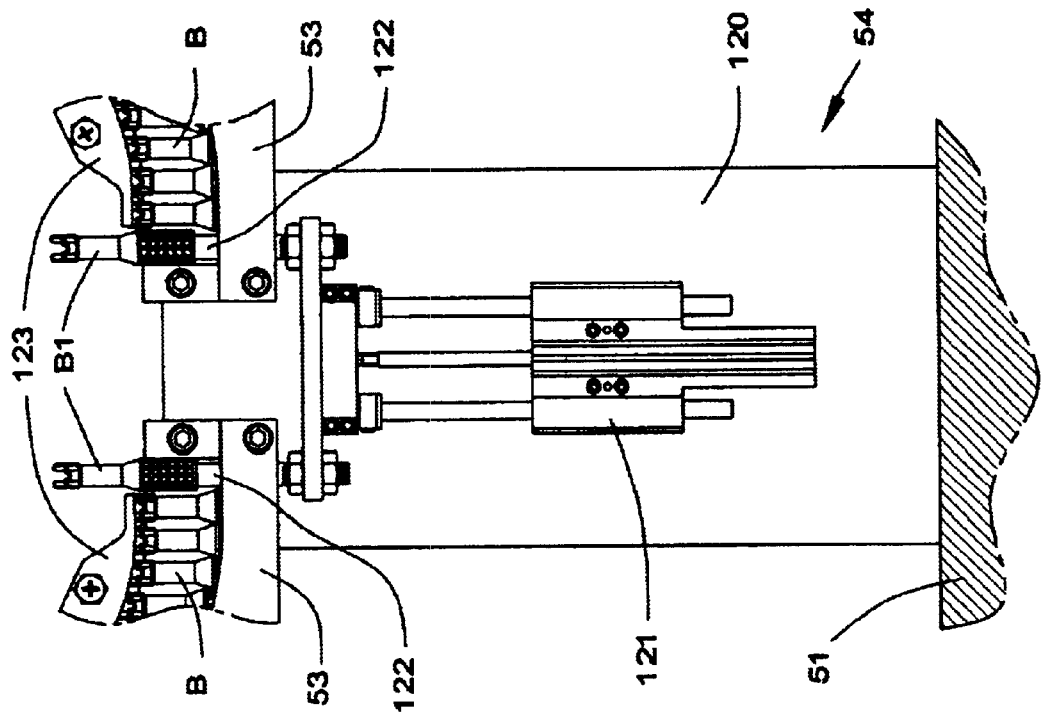
FIG. 9 is a front view of the isolator of Station One illustrated in FIG. 7 with the isolator slide in the "up" position.
Figure 8:
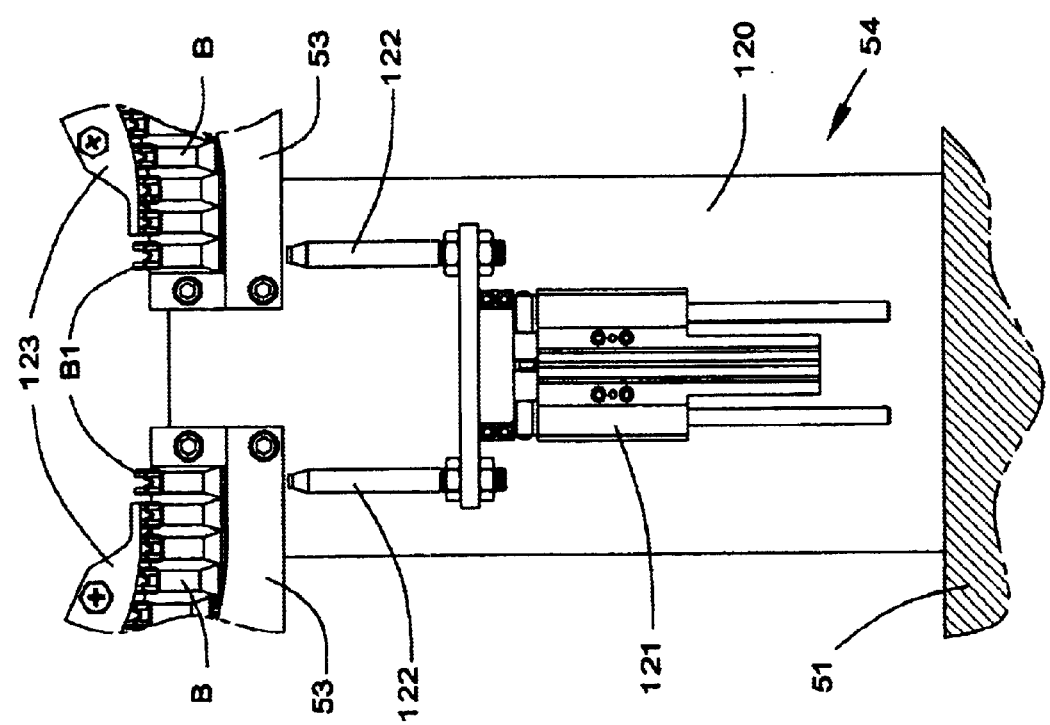
FIG. 8 is a front view of the isolator of Station One illustrated in FIG. 7 with the isolator slide in the "down" position.

Two alignment pins 81, shown in FIGS. 5 & 6, are press fit into holes 82 in the base plate 77. Each alignment pin 81 extends from the base plate 77 to engage a groove 83 in each of the mounting posts 78 to ensure proper alignment of the mounting posts 78 in the fixture 50.

The mounting post 78 includes a lengthwise through hole 84. A pin 85 is slideable in the hole 84 between two positions, "up" and "down", which are defined by two grooves 86 in the pin 85 and a spring-loaded ball plunger 87 mounted at a right angle and with access to the lengthwise hole 84. The ball of the spring-loaded ball plunger 87 engages the grooves 86 in the pin 85 in both the "up" and "down" positions to limit free movement of the pin 85 and prevent the pin 85 from falling out of the mounting post 78. This pin 85 is used to facilitate the lubrication of the drive shaft as discussed in detail below.

Each fixture 50 further includes a mechanism for closing the body of the angle. The housing 90 and two bearing blocks 91 together support a set of four ball bearings 92. These bearings 92, arranged in axial alignment with each other, support a two-piece, cylindrical shaft 93 consisting of a right half 94 and a left half 95. Both halves 94 & 95 include a cut-away section 96 in which approximately ¾ of the shaft material has been removed to provide clearance for both the prophy angle and the gripper fingers that mount the prophy angles onto the posts 78. The cut-away sections 96 of both shaft halves 94 & 95 further include a recess 97 for receiving the closure of the prophy angle body. The two shaft halves 94 & 95 are attached in a male/female relationship and aligned with each other by a roll pin through a hole that extends at a right angle to the axis of the shaft 93 through both of the shaft halves 94 & 95.

Within the housing 90 is a push rod 100 accessible from the front of the housing 90 and slideably supported by two bronze bushings 91 pressed into the housing 90. Mounted to the push rod 100 is a collar block 102 to which is attached a length of roller chain 103. The roller chain 103 wraps around a sprocket 104 mounted in the center of the shaft 93. The other end of the roller chain 103 is attached to an extension spring 105 attached by a pin 106 to the rear of the housing 90. A dust cover 107 is attached to the housing 90 to enclose the components within the housing 90 while providing access to the push rod 100 at the front of the fixture 50.

The push rod 100 is threaded at its rear end extending from the rear of the housing 90. A pair of jam nuts 108 on the threaded end of the push rod 100 is used for precise angular adjustment of shaft 93. An elastic washer 109 is placed on the push rod 100 between the jam nuts 108 and the housing 90 to serve as a shock absorber when the push rod 100 retracts.

Each station 1 thru 16 of the assembly unit 17 performs a different operation in the assembly of the prophy angle. These operations are performed simultaneously as a sequence of four steps. The following is a description of each station and the four steps it performs.

Referring to FIGS. 2 and 7 thru 9, a first feed module 42 feeds angle bodies B to Station One 1. This feed module 42 consists of a steel base 51 similar to the main base 47 described above but sized for mounting two vibratory feeder bowls 52 and two gravity track magazines 53. Two feeder bowls 52 are preferred, one clockwise and the other counterclockwise, so that the angle bodies B can be fed with the desired orientation described below. The feeder bowls 52 and gravity track magazines 53 are mounted on their base 51 such that one set is a mirror image of the other, feeding angle bodies B to Station One 1 from opposite directions.

From the feeder bowls 52, prophy angle bodies B slide down the inclined rails of their respective gravity track magazines 53 to the body isolator 54 at the bottom of the two magazines 53. Angle bodies B accumulate in each magazine 53 until a photoelectric sensor near the top of the magazine senses that the magazine is full, shutting off its feeder bowl.

The weight of the accumulated bodies B in each magazine ensures that the body B1 at the bottom of the magazine is properly positioned in the isolator 54. A containment rail 123 in each magazine 53 prevents the bodies B from climbing over one another or falling out of the magazine.

The body isolator 54 consists preferably of a welded steel frame 120. Both of the body magazines 53 are mounted to the isolator frame 120 such that the bodies B1 at the end of each magazine 53 are hanging parallel to each other, side by side, and spaced apart a distance equal to the distance between the mounting posts 78. Mounted to the isolator frame 120 directly below the ends of the magazines 53 is an air-driven slide 121 to which a pair of studs 122 is attached. Each stud 122 is positioned in axial alignment with one of the bodies B1 hanging above and sized to fit loosely within the Doriot opening of the body.

Figure 10:
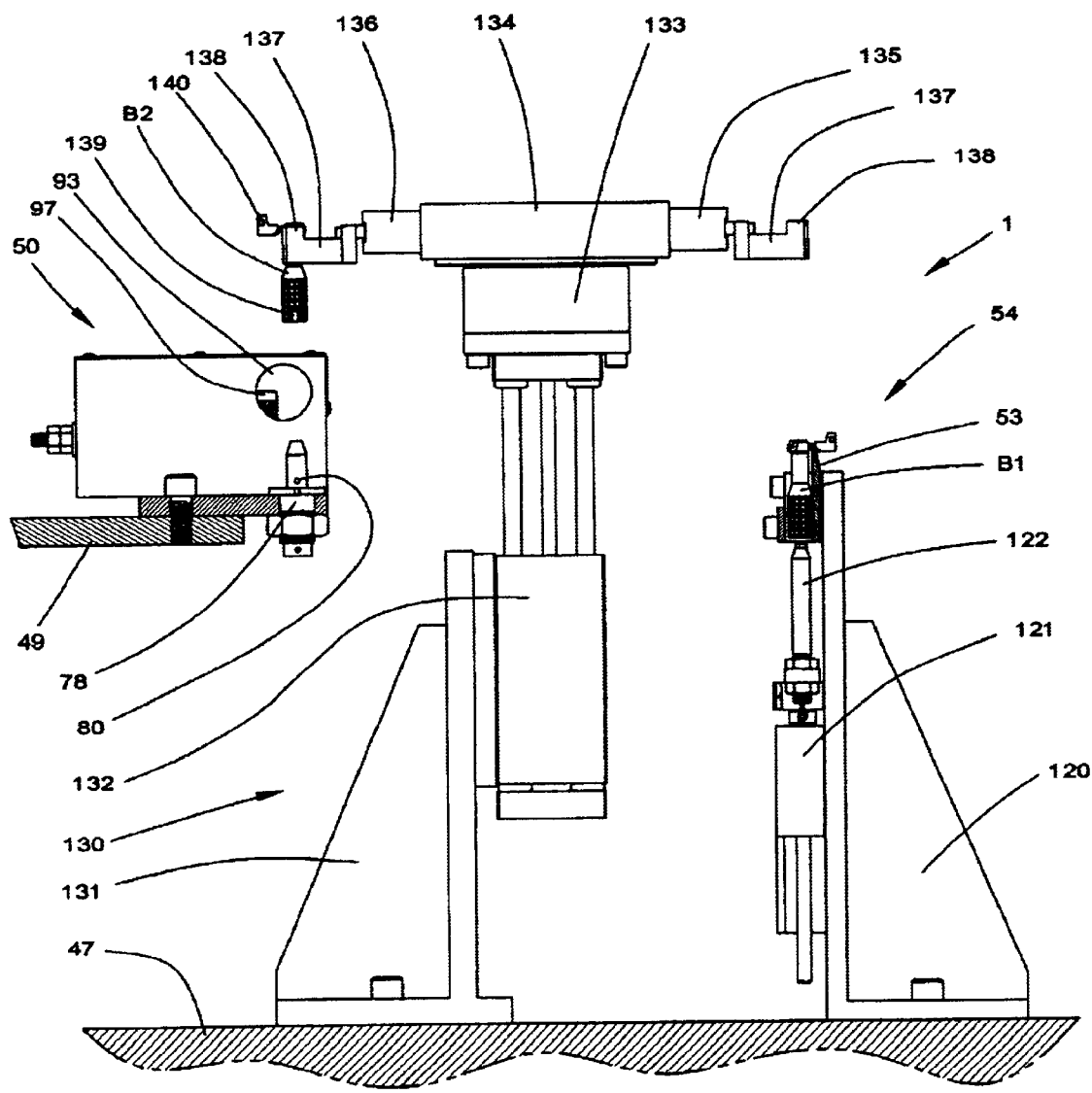
FIG. 10 is a side view of Station One illustrated in FIG. 7 with the pick-and-place in the "up" position and the isolator slide in the "down" position.
Figure 11:
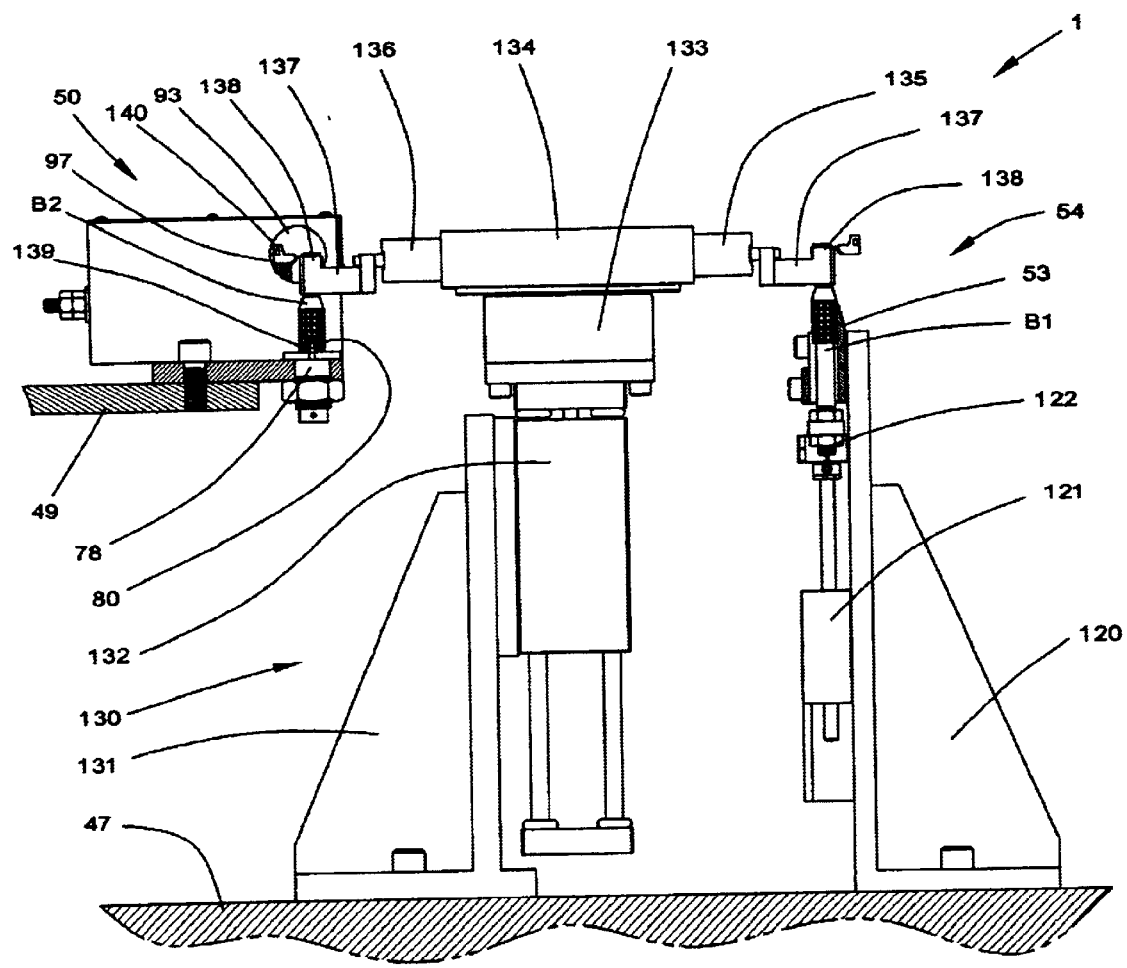
FIG. 11 is a side view of Station One illustrated in FIG. 7 with the pick-and-place in the "down" position and the isolator slide in the "up" position.

Referring to FIGS. 2, 10 and 11, a pick-and-place unit 130 is mounted to the main base 47 at Station One 1 between the body isolator 54 and the dial plate 49. The pick-and place unit 130 consists of a welded steel frame 131 to which is mounted an air-driven slide 132 to provide up and down motion of about three inches. Mounted on top of the slide 132 is an air-driven, 180° rotary actuator 133 to which is attached a gripper mounting plate 134 with two pairs of air-driven, parallel grippers 135 and 136. Air is supplied to the four grippers such that when the first pair 135 is open, the second pair 136 is closed and vice-versa. Each of the four grippers 135 and 136 is equipped with a pair of fingers 137 shaped for clamping the neck of an angle body B1. The gripper fingers 137 include an extension 138 that makes contact with the non-cylindrical portion of the body B1 to ensure proper orientation during the transfer from the isolator to the fixture 50.

Station One 1 performs the operation of loading bodies B1 into the fixtures 50 on the dial plate 49 as follows:

Step 1: The isolator slide 121 extends to its "up" position causing the isolator studs 122 to engage, from below, the two bodies B1 hanging at the end of each magazine 53 in the isolator 54. The two bodies B1 are lifted from the magazines 53 by the studs 122 to an isolated position approximately 1½ inches above the magazines 53. The containment rails 123 are sized to allow only the bodies B1 at the end of the magazines 53 to be lifted by the studs 122. Simultaneously, the pick-and-place 130 lowers to its "down" position where two bodies B2 already held by the closed pair of grippers 136 are placed onto the mounting posts 78 of an empty fixture 50 on the dial plate 49. The slots 139 in the bodies B2 engage the keys 80 on the mounting posts 78, and the body closures 140 rest in the recesses 97 of the shaft 93. This downward motion also places the open grippers 135 in position to grip the two bodies B1 lifted by the isolator 54.

Step 2: Sensors verify these motions so that immediately upon completion, the two grippers 135 at the isolator 54 close, gripping two bodies B1 while the two grippers 136 at the fixture 50 open, releasing two bodies in the fixture 50.

Step 3: The pick-and-place 130 lifts, removing the two bodies B1 from the studs 122 of the isolator 54 and leaving two bodies B2 on the mounting posts 78 in the fixture 50. At the same time, the isolator slide 121 retracts to its "down" position, lowering the studs 122, which creates an open space at the end of each magazine 53. The weight of the bodies B in each magazine 53 causes the bodies B to slide down, filling the two open spaces with the next body B in each line.

Step 4: When sensors detect the completion of Step 3, the rotary actuator 133 rotates 180°, transferring the bodies B1 from a position directly above the isolator 54 to a position directly above the mounting posts 78 in a fixture 50 on the dial plate 49. Simultaneously, the dial plate 49 indexes one position, moving the fixture 50 at Station One 1 to Station Two 2 and introducing an empty fixture 50 to Station One 1.

Figure 12:
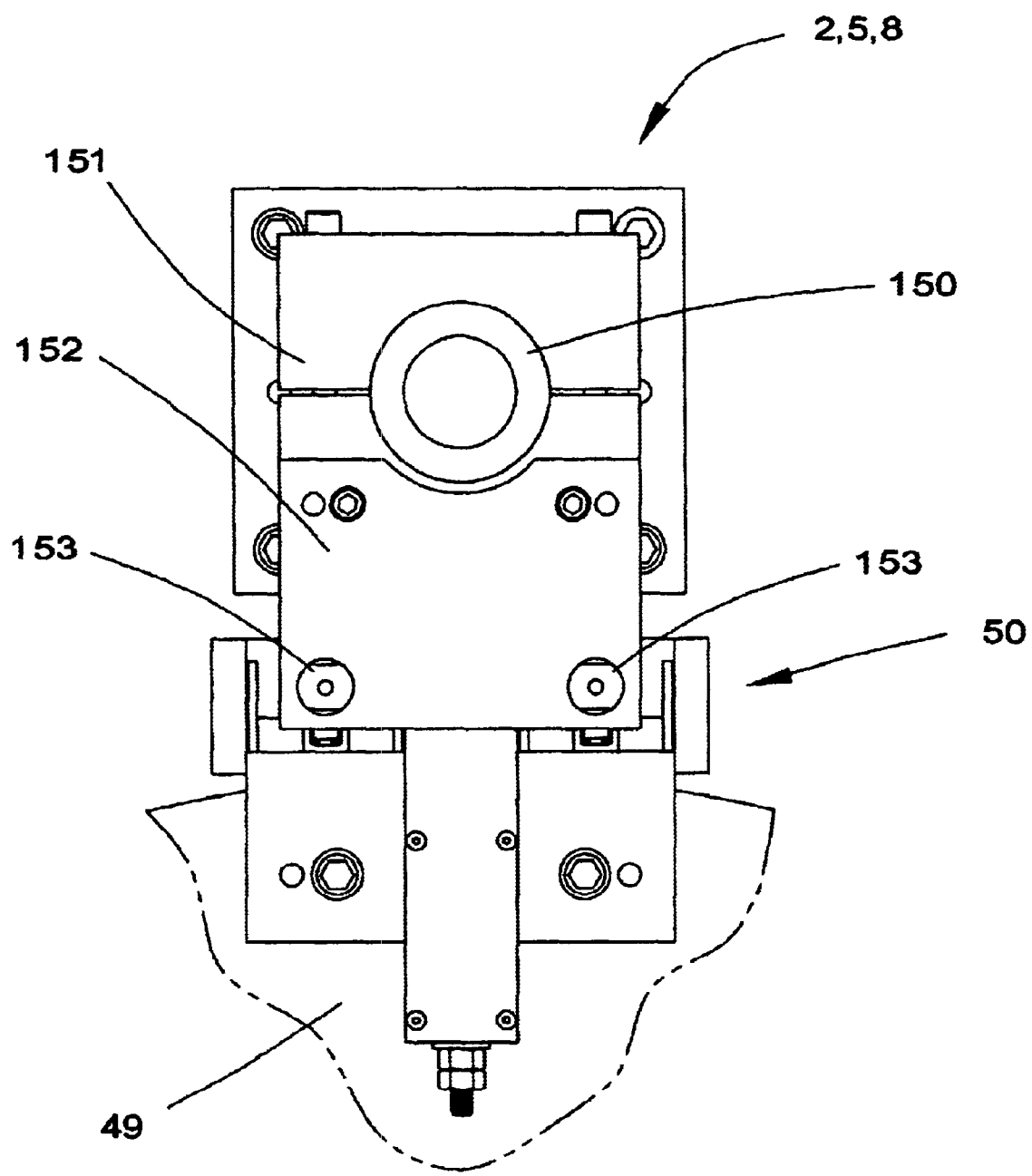
FIG. 12 is a plan view of Stations Two, Five, and Eight of the preferred embodiment.
Figure 13:
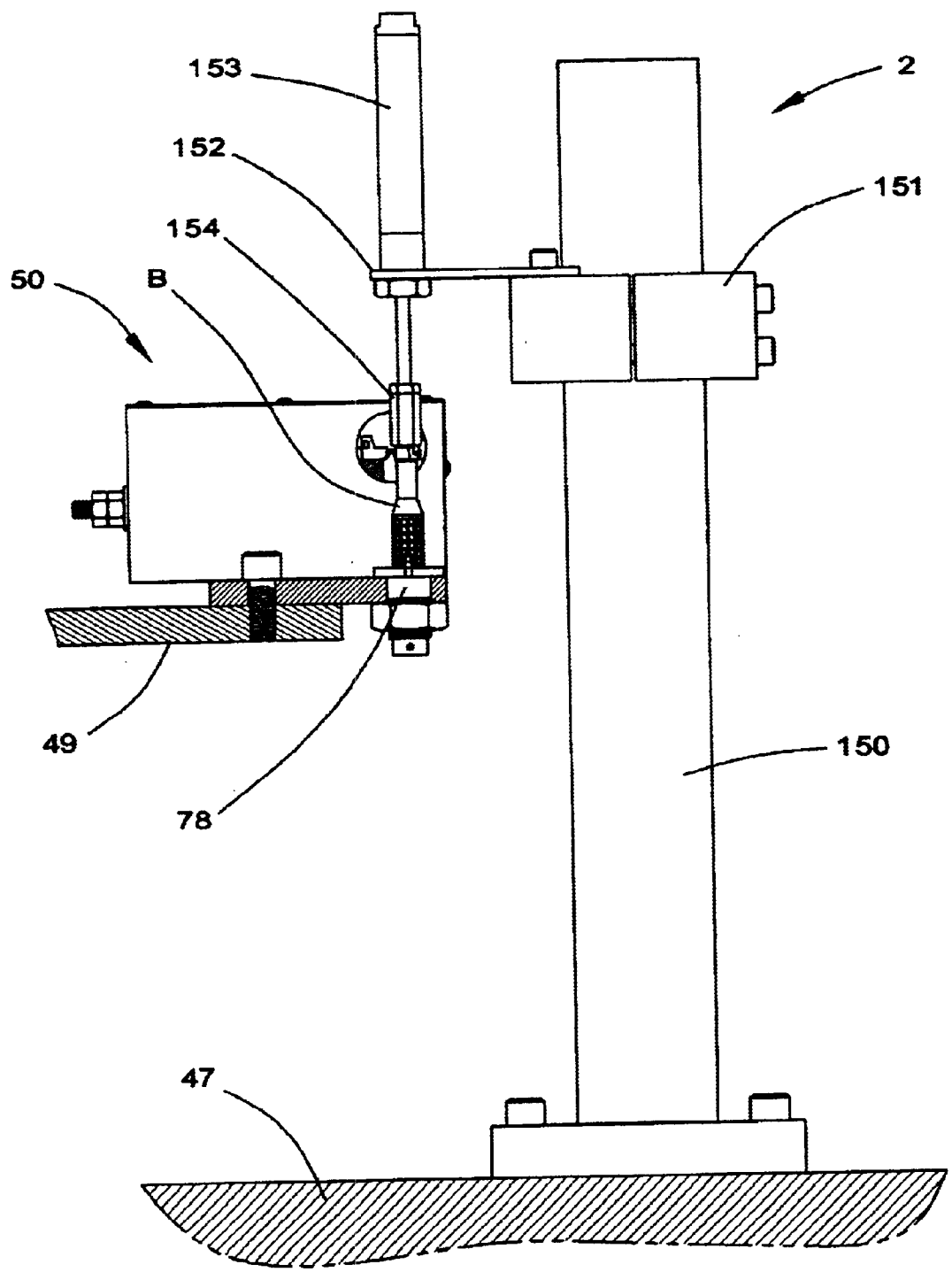
FIG. 13 is a partially cross-sectioned side view of Station Two shown in FIG. 12.
Figure 14:
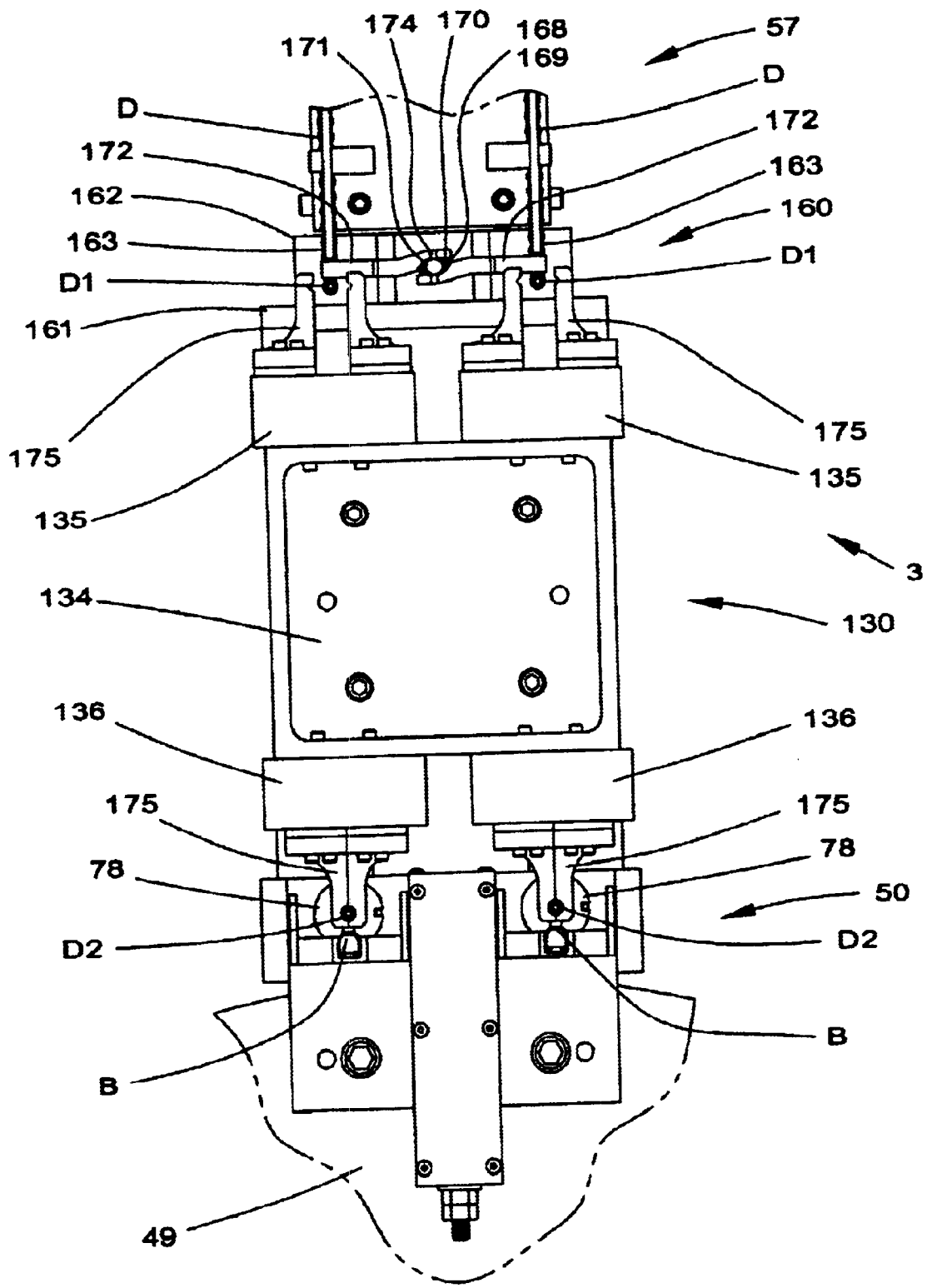
FIG. 14 is a plan view of Station Three of the preferred embodiment.
Figure 15:
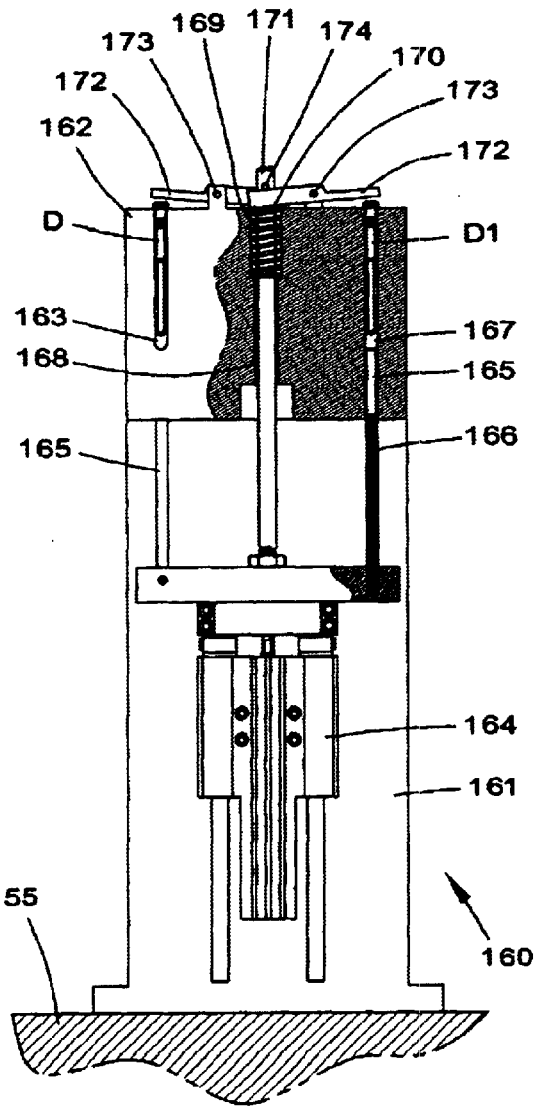
FIG. 15 is a partially cross-sectioned front view of the isolator of Station Three shown in FIG. 14 with the isolator slide in the "down" position.
Figure 16:
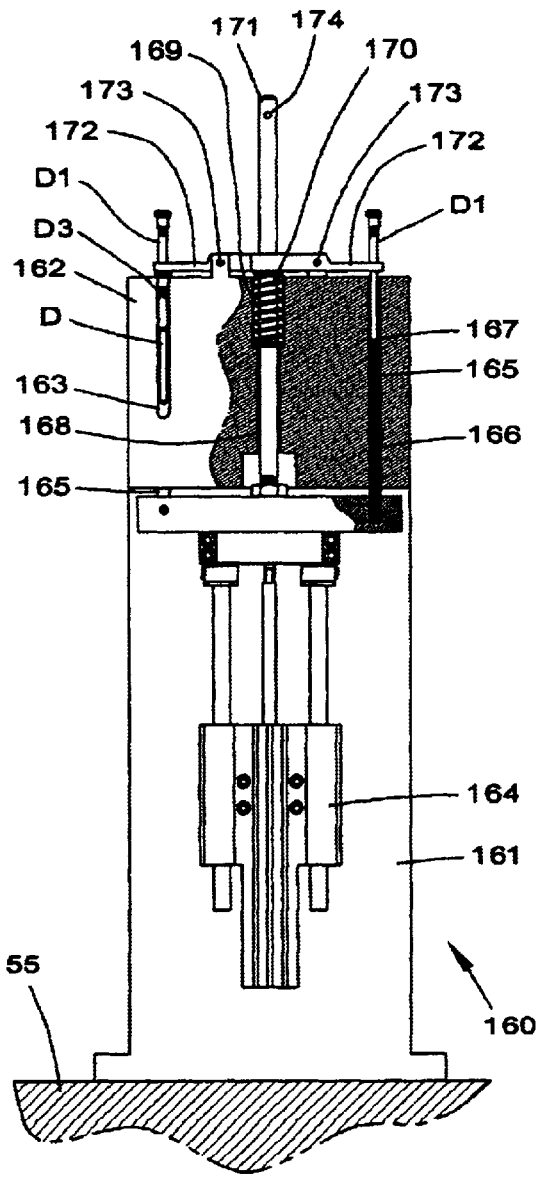
FIG. 16 is a partially cross-sectioned front view of the isolator of Station Three shown in FIG. 14 with the isolator slide in the "up" position.
Figure 17:
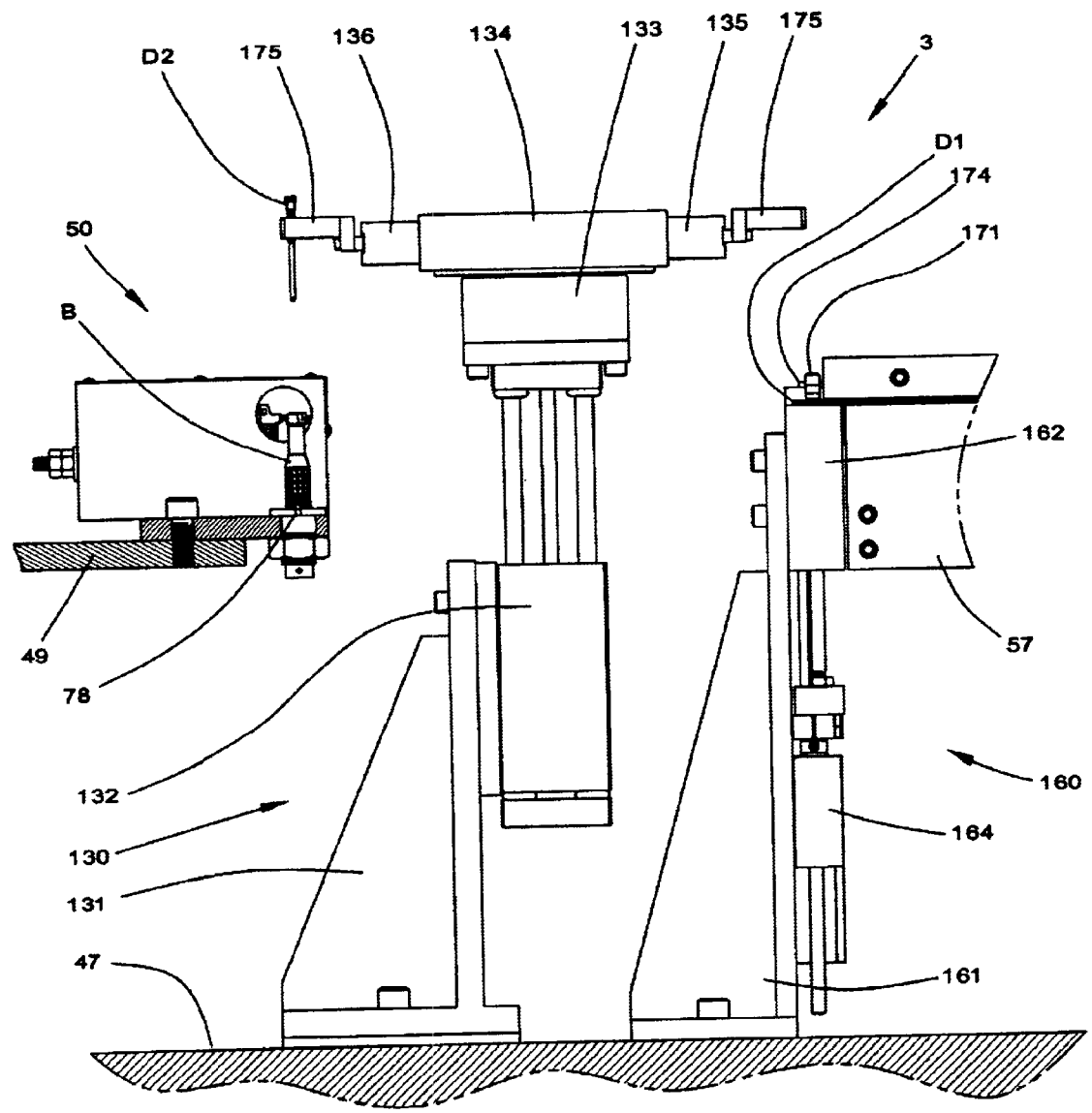
FIG. 17 is a partially cross-sectioned side view of Station Three shown in FIG. 14 with the pick-and-place mechanism in the "up" position and the isolator in the "down" position.

Referring to FIGS. 12 and 13, a support post 150 is mounted to the main base 47 at Station Two 2. Attached to the support post 150 is a clamp block 151 to which a cylinder mounting plate 152 is fastened. The cylinder mounting plate 152 supports a pair of air cylinders 153 vertically aligned directly above the bodies B in the fixture 50 at Station Two 2. Each air cylinder 153 is fitted with a tip 154 sized to make contact with the exposed brim of the gear chamber of the body B for pushing it onto the mounting post 78.

Station Two 2 performs the operations of securing bodies B in the fixture 50 and verifying the presence of the bodies as follows:

Step 1: The air cylinders 150 extend causing the tips 154 to make contact with the bodies B, shoving the bodies B downward onto the mounting posts 78.

Step 2: If a body B is not present on the mounting post 78, the corresponding air cylinder 150 extends farther than if the body B is present. If this happens, a sensor detects this condition stopping the machine and sounding an alarm to notify the operator.

Step 3: The two air cylinders 150 retract.

Step 4: The dial plate 49 indexes, moving the fixtures 50 one position to the next station.

At Station Three 3, the drive shaft is inserted into the prophy angle body. Referring to FIG. 2, the drive shaft feed module 43 feeds drive shafts to Station Three 3. This feed module 43 consists of a steel base 55 similar to the main base 47 described above but sized for mounting a dual-line vibratory feeder bowl 56 and a dual in-line vibratory feeder 57. Dual-line feeders are used so that drive shafts can be fed in pairs to the station. Drive shafts are oriented in the feeder bowl 56 and fed diameter to diameter, hanging by the gear to the in-line feeder 57, which also serves as a magazine to the drive shaft isolator 160 shown in FIGS. 14 thru 18.

Referring to FIGS. 14 thru 18, the drive shaft isolator 160 includes a welded steel frame 161 machined and mounted to the main base 47 at Station Three 3. An isolator block 162 machined with two slots 163 for receiving drive shafts D from the in-line feeder 57 is attached near the top of the frame 161. The in-line feeder 57 feeds a pair of drive shafts D into the slots 163 in the isolator block 162. In the isolator block 162 two drive shafts D1 hang parallel to each other, side by side, spaced apart a distance equal to the distance between the mounting posts 78. Mounted to the isolator frame 161 directly below the isolator block 162 is an air-driven slide 164 to which a pair of tubes 165 is attached in axial alignment with the first pair of the drive shafts D1 hanging above. A pin 166 located inside each of the two tubes 165 are sized approximately one inch shorter than the tubes 166. Two holes 167 in the isolator block 162 provide a passage for each tube 165 to its respective slot 163.

The isolator block 162 includes a through hole 168 centered between the slots 163. This hole 168 includes a counter bore 169 sized for housing a compressed spring 170. A rod 171 attached to the air-driven slide 164 between the tubes 165 extends through the hole 168 and the spring 170 in the isolator block 162. A pair of containment arms 172 is pivotably mounted by pins 173 on top of the isolator block 162, one on each side of the rod 171 such that the compressed spring 170 applies constant pressure on the containment arms 172. The containment arms 172 are positioned in alignment with the second pair of drive shafts D3 in the isolator block. When the slide 164 is in the "up" position, the force of the spring 170 traps the second pair of drive shafts D3 under the containment arms 172 to prevent the shafts D3 from moving. The rod 171 includes a cross pin 174 that makes contact with the containment arms 172 when the air-driven slide 164 is in the "down" position thereby allowing drive shafts D3 to pass freely under the containment arms 172 only when the slide 164 is in the "down" position.

A pick-and-place unit 130 is mounted to the main base 47 at Station Three 3 between the drive shaft isolator 160 and the dial plate 49. The pick-and-place unit 130 at Station Three 3 is identical to the pick-and-place 130 at Station One 1 described above except for the gripper fingers 175 which are shaped to grip drive shafts instead of bodies.

Figure 18:
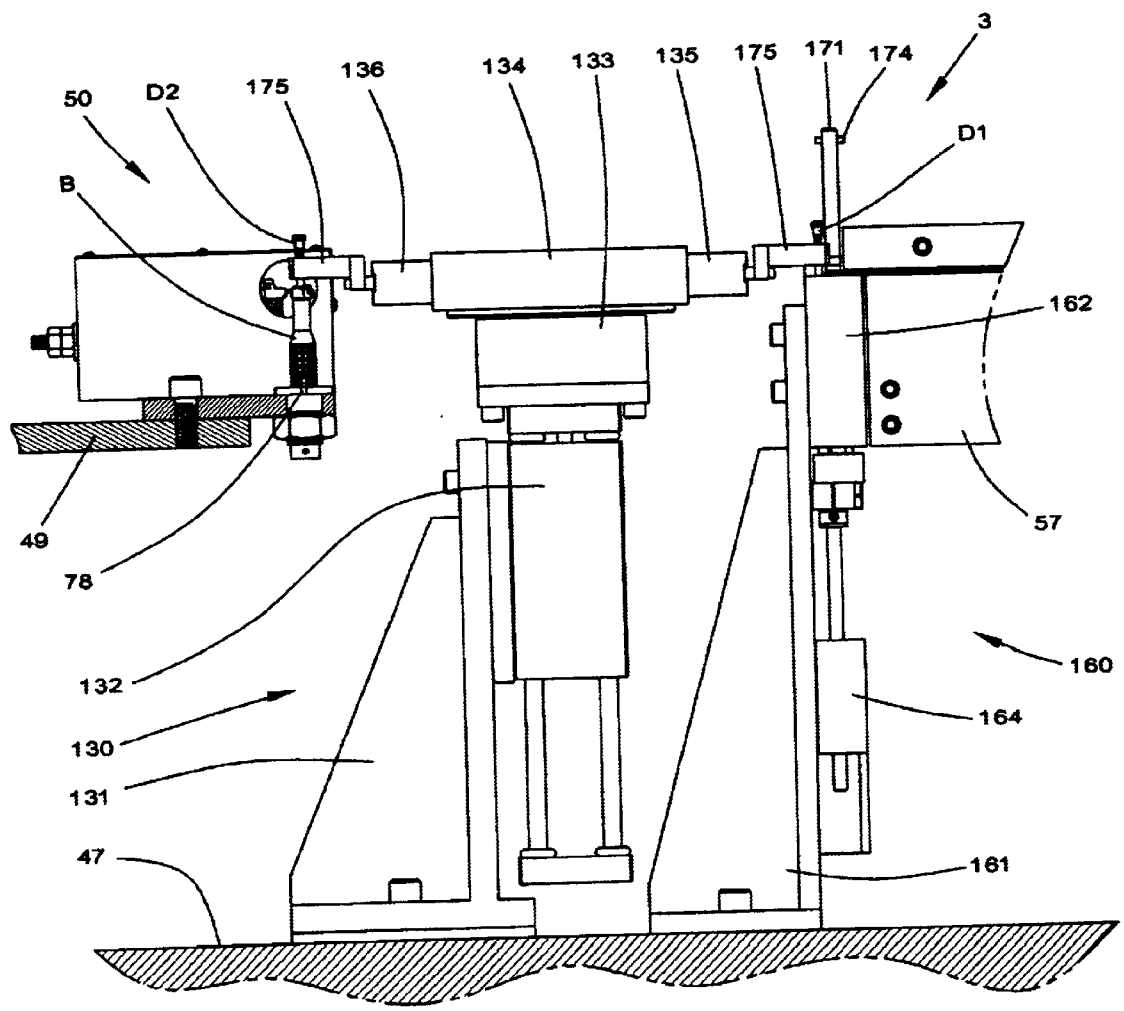
FIG. 18 is a partially cross-sectioned side view of Station Three shown in FIG. 14 with the pick-and-place mechanism in the "down" position and the isolator in the "up" position.

At Station Three 3, drive shafts are inserted into the bodies as follows:

Step 1: The isolator slide 164 extends to its "up" position, shown in FIGS. 16 and 18, causing the tubes 165 to engage, from below, the two drive shafts D1 hanging in the isolator block 162. At the same time, the containment arms 172 trap the second pair of drive shafts D3 to prevent the feeding shafts D from advancing. The drive shafts D1 are lifted in the isolator 160 by the pins 166 and supported by the tubes 165 to extend approximately one inch above the isolator block 162. Simultaneously, and as shown in FIG. 18, the pick-and place 130 lowers to its "down" position where two drive shafts D2 already held by the closed pair of grippers 136 are placed into a pair of bodies B in the fixture 50 on the dial plate 49. This downward motion also places the open grippers 135 in position to grip the two shafts D1 lifted by the isolator 160.

Step 2: Sensors verify these motions so that immediately upon completion, the two grippers 135 at the isolator 160 close, gripping two drive shafts D1 in the isolator 160. At the same time, the two grippers 136 at the fixture 50 open, releasing two drive shafts D2 in the bodies B in the fixture 50.

Step 3: The pick-and-place 130 lifts, removing the two drive shafts D1 from the isolator 160 and leaving two drive shafts D2 in the bodies B in the fixture 50. At the same time, the isolator slide 164 retracts to its "down" position, lowering the tubes 165, creating a vacancy in the isolator slot 164, and releasing the next pair of drive shafts D3 in the isolator block 162. The vibratory in-line feeder 57 advances the drive shafts D forward, filling the two open spaces with the next drive shaft D in each line.

Step 4: When the pick-and-place 130 reaches the "up" position, the rotary actuator 133 rotates 180° transferring the drive shafts D1 from a position directly above the isolator 160 to a position directly above the bodies B in a fixture 50 on the dial plate 49. Simultaneously, the dial plate 49 indexes, moving the fixtures 50 one position to the next station.

At Station Four 4 and Station Six 6, the angles are lubricated. A food grade, viscous lubricant such as petroleum jelly is preferred and is fed to both of these stations by the lubricant-dispensing module 46 shown in FIG. 2. The lubricant dispensing module 46 consists of a thermally insulated, heated, stainless steel tank 58. Air pressure is applied to the tank 58 to force the petroleum jelly through heated, insulated, flexible, feed lines 181 to Station Four 4 and Station Six 6 shown in FIGS. 19 and 21.

Two air-operated dispensing valves 182 are attached to the end of each feed line 181 so that the nozzles 183 of the two valves 182 are spaced apart a distance equal to the distance between the mounting posts 78 in the fixtures 50. The dispensing valves 182 are attached to an air-driven slide 184 mounted to extend toward the center of the dial plate 49 at a 45° angle from horizontal. The entire assembly is mounted to the main base 47 by a support post 150 and clamp 151.

Figure 19:
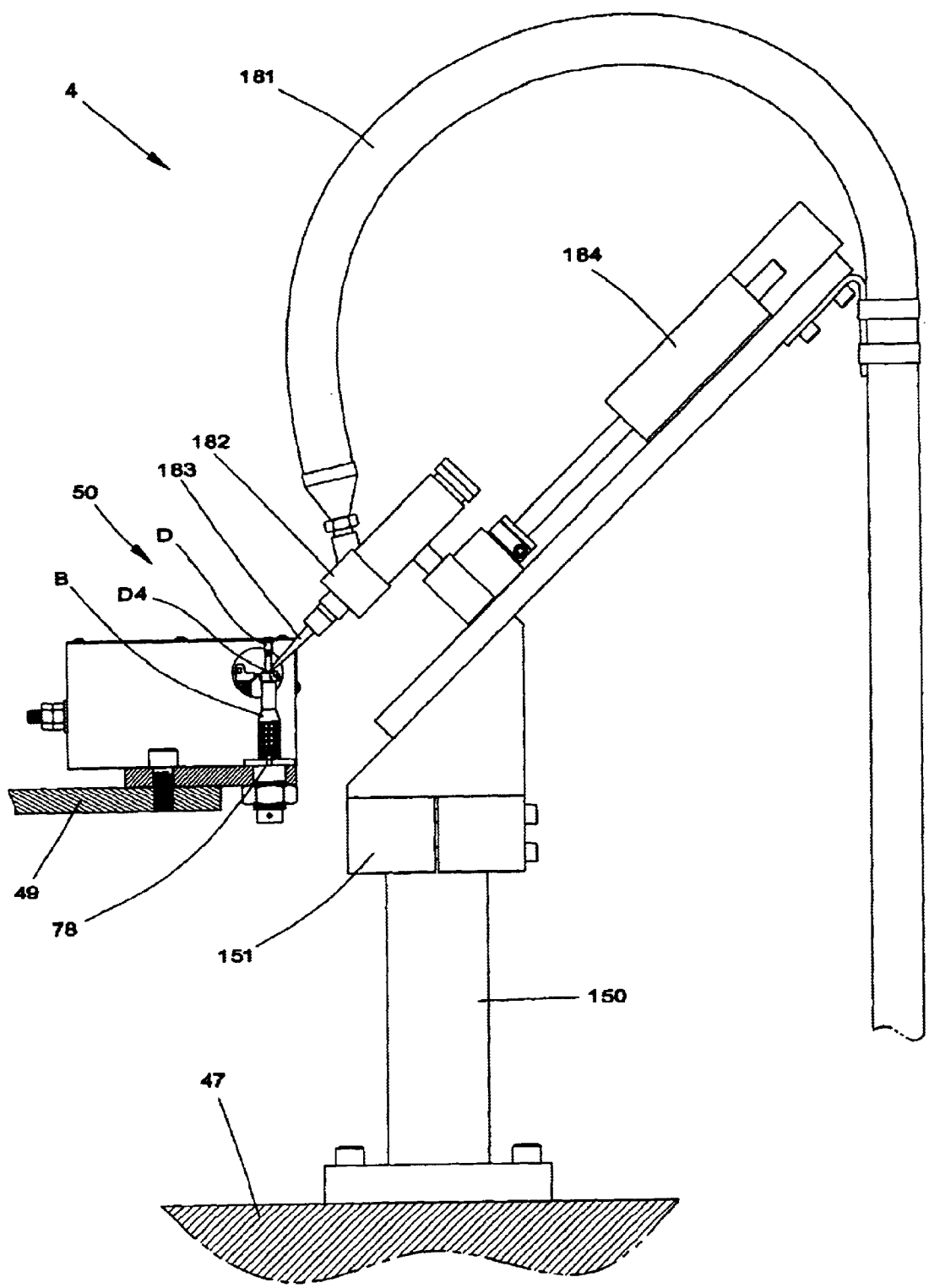
FIG. 19 is a side view of Station Four of the preferred embodiment.

At Station Four 4, the drive shafts D are in the bodies B held in an intermediate position, as shown in FIG. 19, by the pins 85 (see FIG. 6) inside the mounting posts 78. In this intermediate position, the drive shafts D extend approximately ⅝ of an inch above the bodies B allowing access to the lower drive shaft bearings D4 for lubrication as follows:

Step 1: The air-driven slide 184 extends placing the nozzles 183 of the two dispensing valves 182 in the fixture 50 in close proximity to the lower bearings D4 of the two drive shafts.

Step 2: The dispensing valves 182 are actuated allowing the flow of lubricant from the nozzles 183 onto the lower drive shaft bearings D4.

Step 3: The air-driven slide 184 retracts removing the nozzles 183 from the fixture 50.

Step 4: The dial plate 49 indexes, moving the fixtures 50 one position to the next station.

Figure 20:
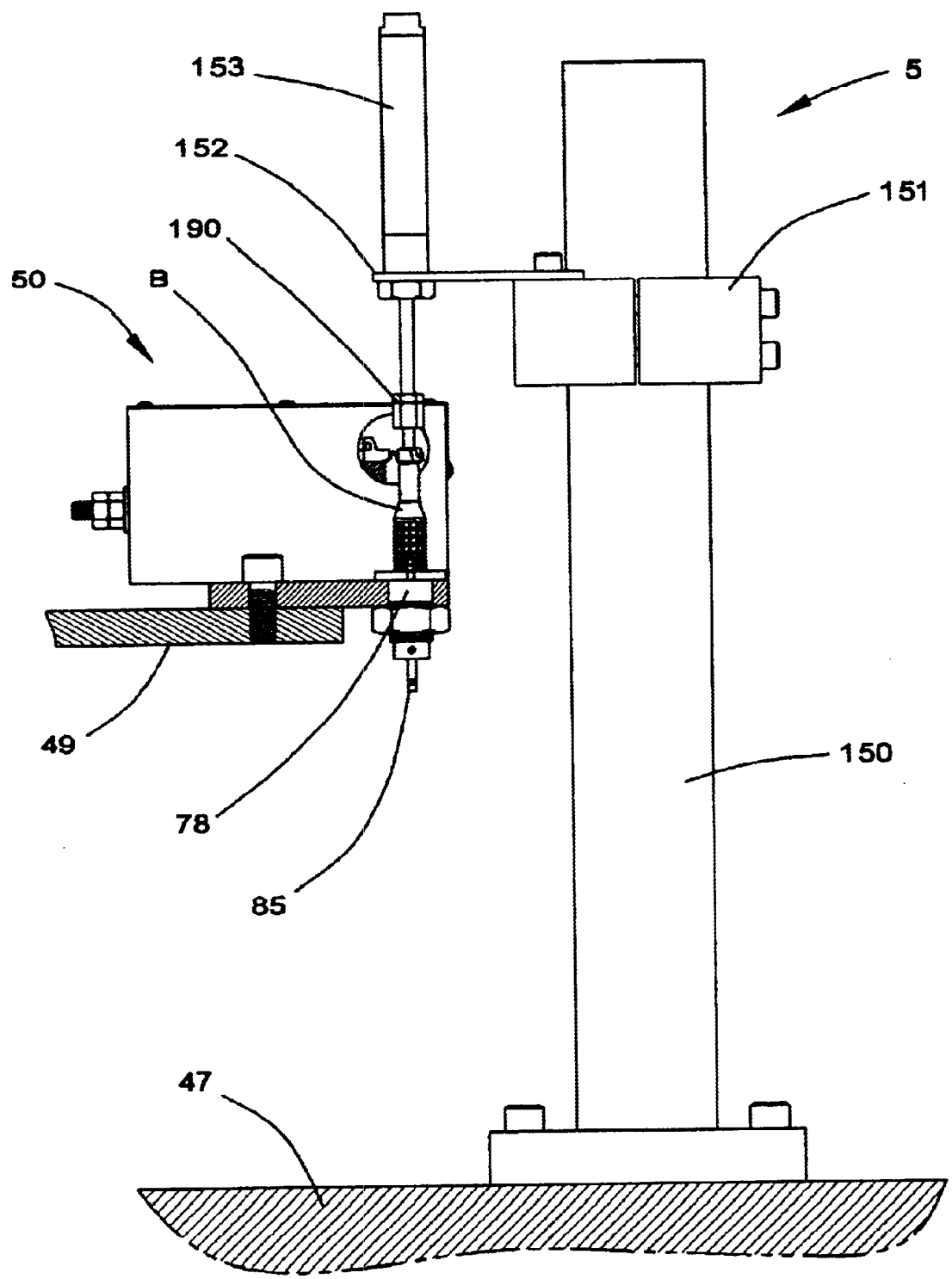
FIG. 20 is a partially cross-sectioned side view of Station Five shown in FIG. 12.

At Station Five 5, the drive shaft is secured in the body of the angle. Referring to FIGS. 12 and 20, this station is identical in construction and operation to Station Two 2 described above. However, referring to FIG. 20, the air cylinder tips 190 are sized to fit within the gear chamber of the body B to ensure that the drive shafts D are fully installed.

Station Five 5 performs as follows:

Step 1: The air cylinders 153 extend downward shoving the two drive shafts D into the bodies B below. As a result, the pins 85 extend downward from the bottom of the mounting posts 78.

Step 2: No action occurs.

Step 3: The air cylinders 153 retract.

Step 4: The dial plate 49 indexes moving the fixtures 50 one position to the next station.

Figure 21:
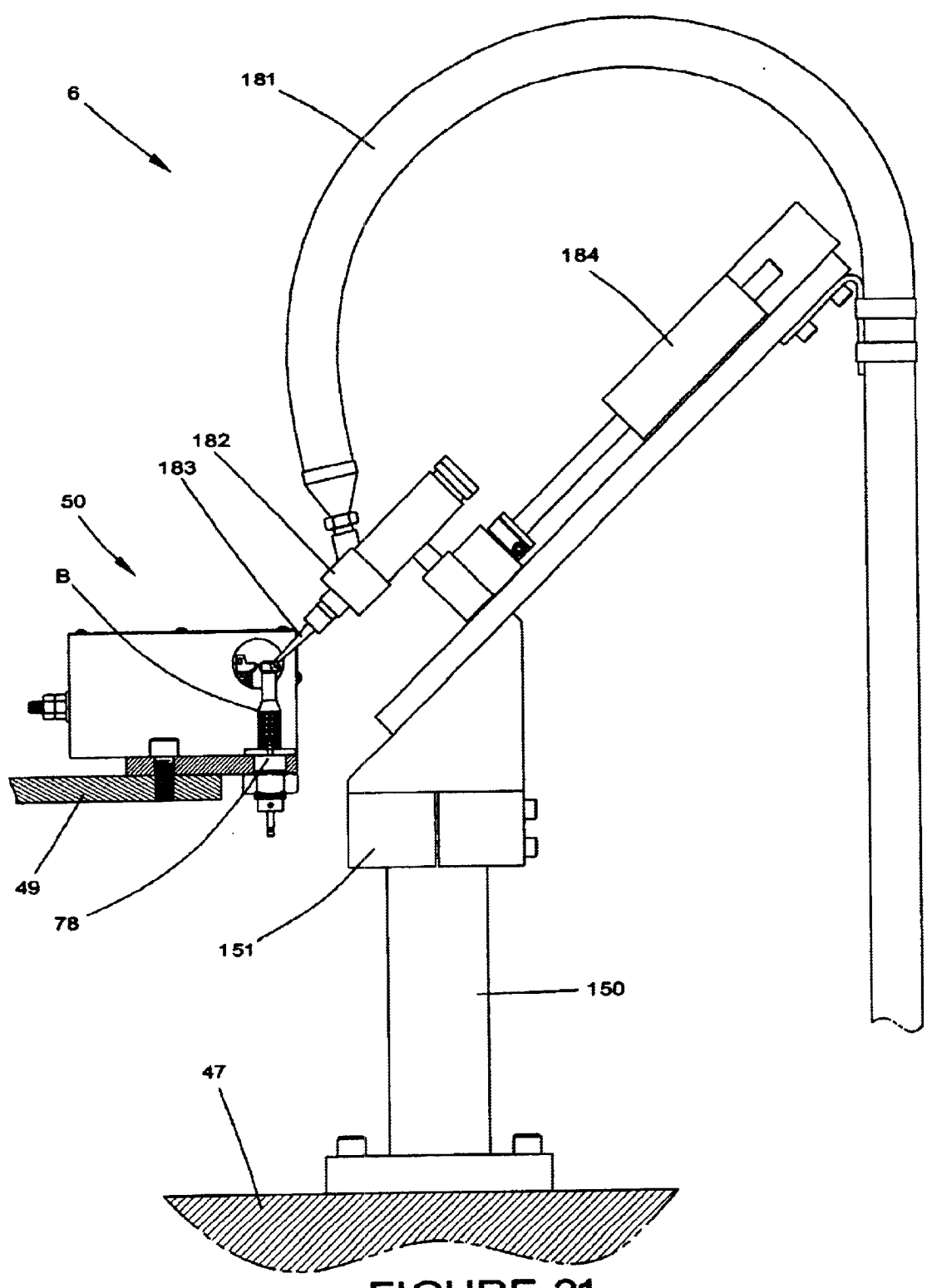
FIG. 21 is a side view of Station Six of the preferred embodiment.

Station Six 6, shown in FIG. 21, is identical in construction and performance to Station Four 4 described above. At Station Six 6, however, since the drive shaft D is fully installed in the body B, the gears of the drive shafts are lubricated instead of the bearings.

At Station Seven 7, the rotor is inserted into the body. Referring to FIG. 2, a feed module 44 feeds rotors to Station Seven 7. This feed module 44 consists of a steel base 59 similar to the main base 47 described above but sized for mounting a vibratory feeder bowl 60 and an in-line vibratory feeder 61. Both the feeder bowl 60 and the in-line feeder 61 are dual-line feeders so that the rotors can be fed in pairs to the station 7. Rotors are oriented in the feeder bowl 60 and fed diameter to diameter, hanging by the flange to the in-line feeder 61, which also serves as a magazine, to the rotor isolator 200 shown in FIGS. 22 THRU 26.

The rotor isolator 200 includes a welded steel frame 201 mounted at Station Seven 7. An isolator block 202 containing a pair of tracks 203 for receiving rotors R from the in-line feeder 61 is attached near the top of the frame 201. The in-line feeder 61 feeds rotors R into the two tracks 203 of the isolator 200. The tracks 203 curve downward and outward reorienting the rotors R axis horizontal, spaced apart a distance equal to the distance between the mounting posts 78 in the fixture 50. From this position 204 the tracks 203 make a sharp, right angle turn upward that, due to gravity, is too abrupt for the rotors R to follow.

Mounted to the isolator frame 201 directly below the isolator block 202 is an air-driven slide 205 to which a pair of studs 206 is attached in axial alignment with the first pair of the rotors R1 in the tracks 203 above. Two holes 207 in the isolator block 202 provide a passage for each of the studs 206 to the rotors R1.

Figure 22:
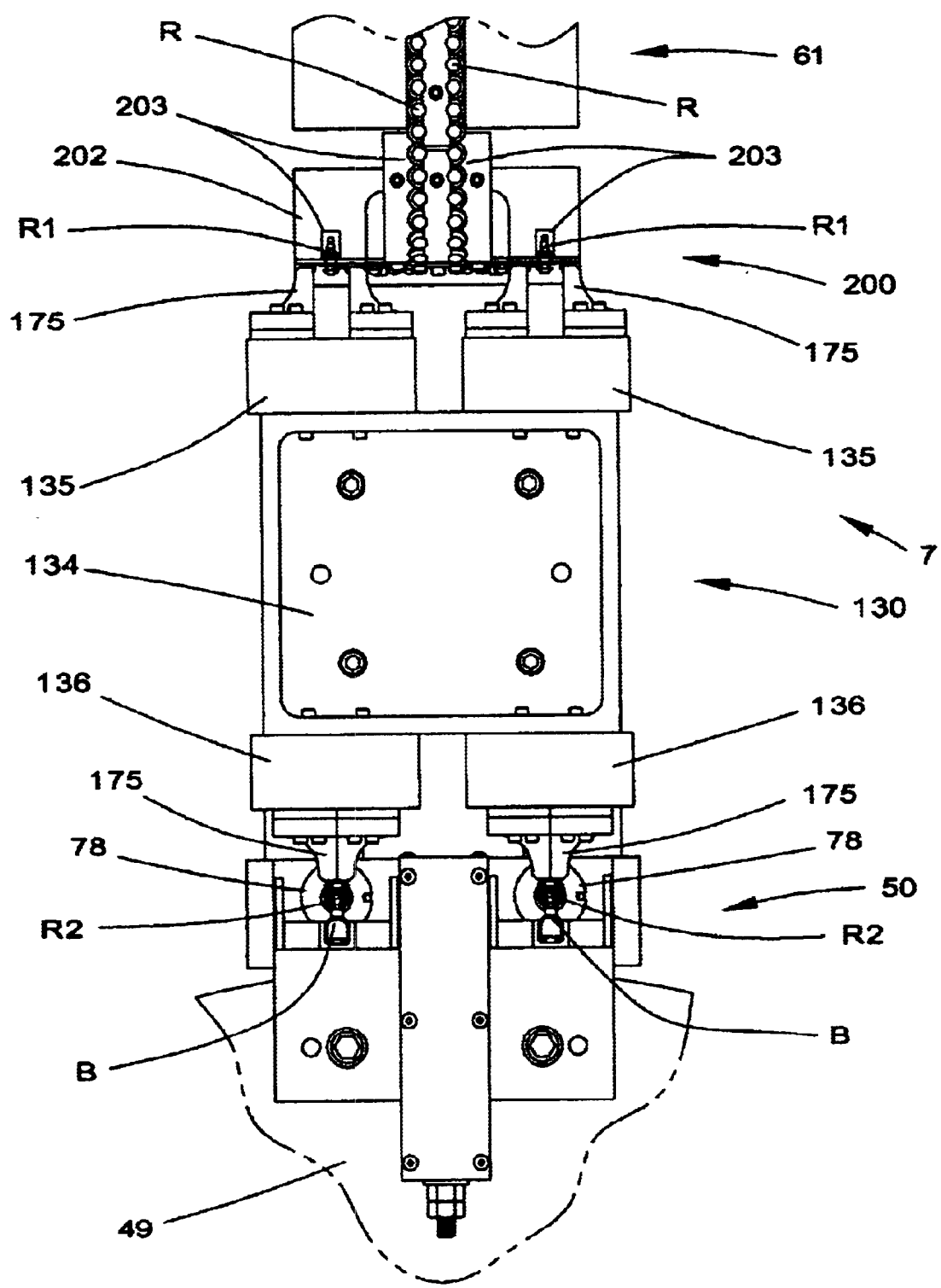
FIG. 22 is a plan view of Station Seven of the preferred embodiment.
Figure 23:
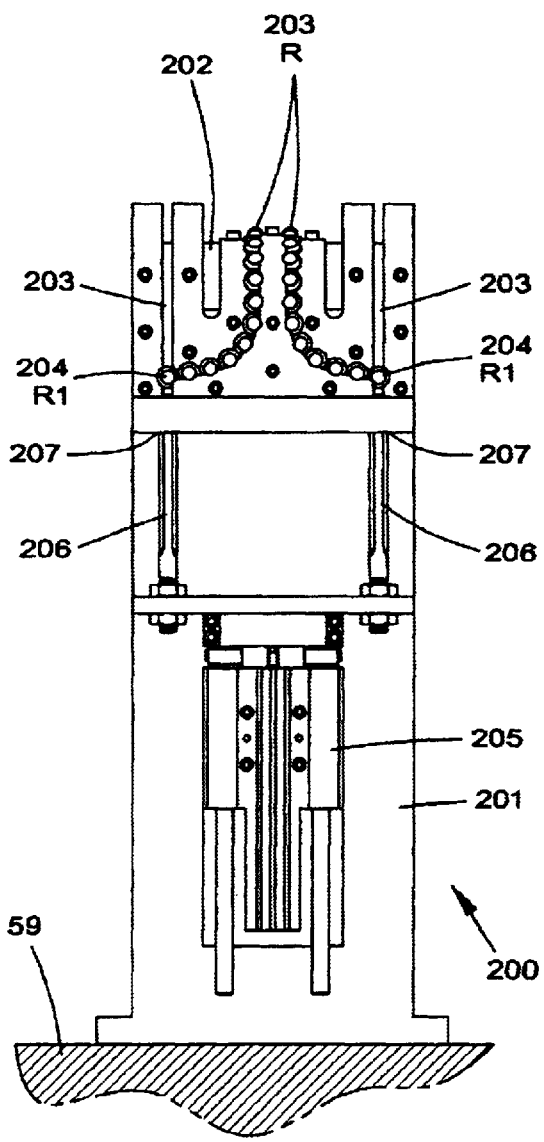
FIG. 23 is a front view of the isolator of Station Seven shown in FIG. 22 with the isolator slide in the "down" position.
Figure 24:
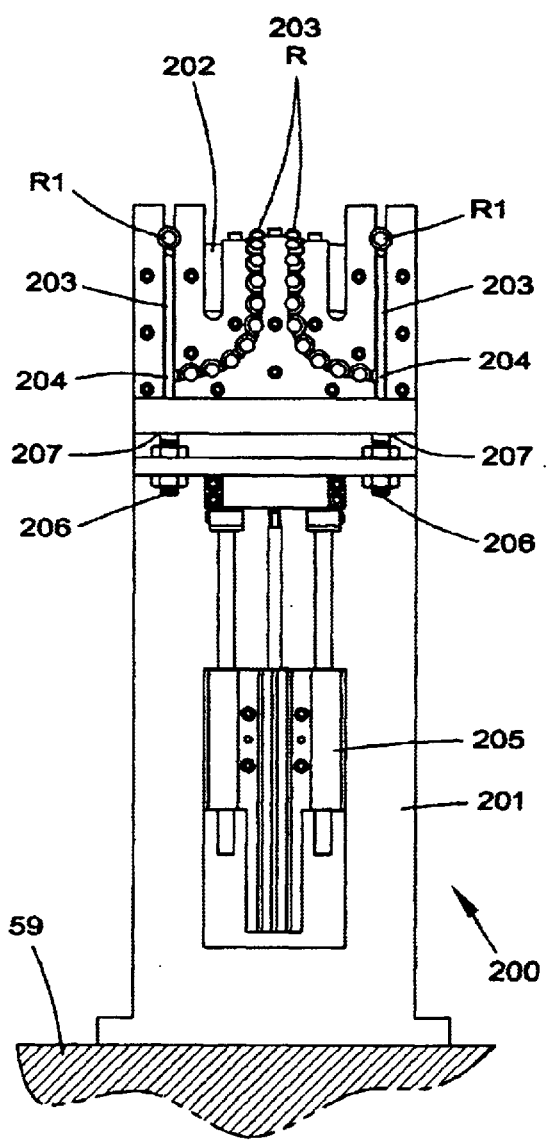
FIG. 24 is a front view of the isolator of Station Seven shown in FIG. 22 with the isolator slide in the "up" position.
Figure 25:
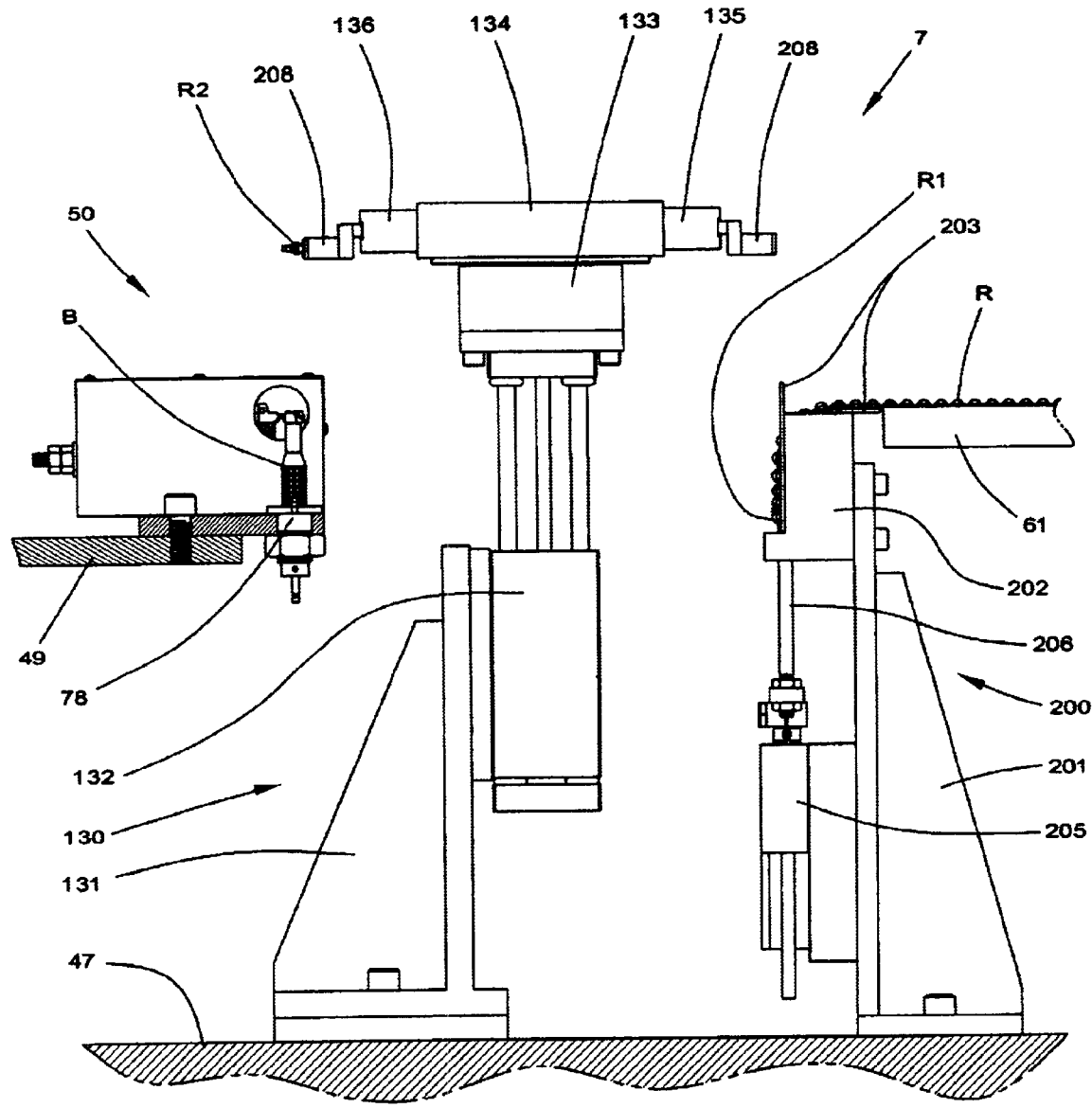
FIG. 25 is a partially cross-sectioned side view of Station Seven shown in FIG. 22 with the pick-and-place mechanism in the "up" position and the isolator slide in the "down" position.
Figure 26:
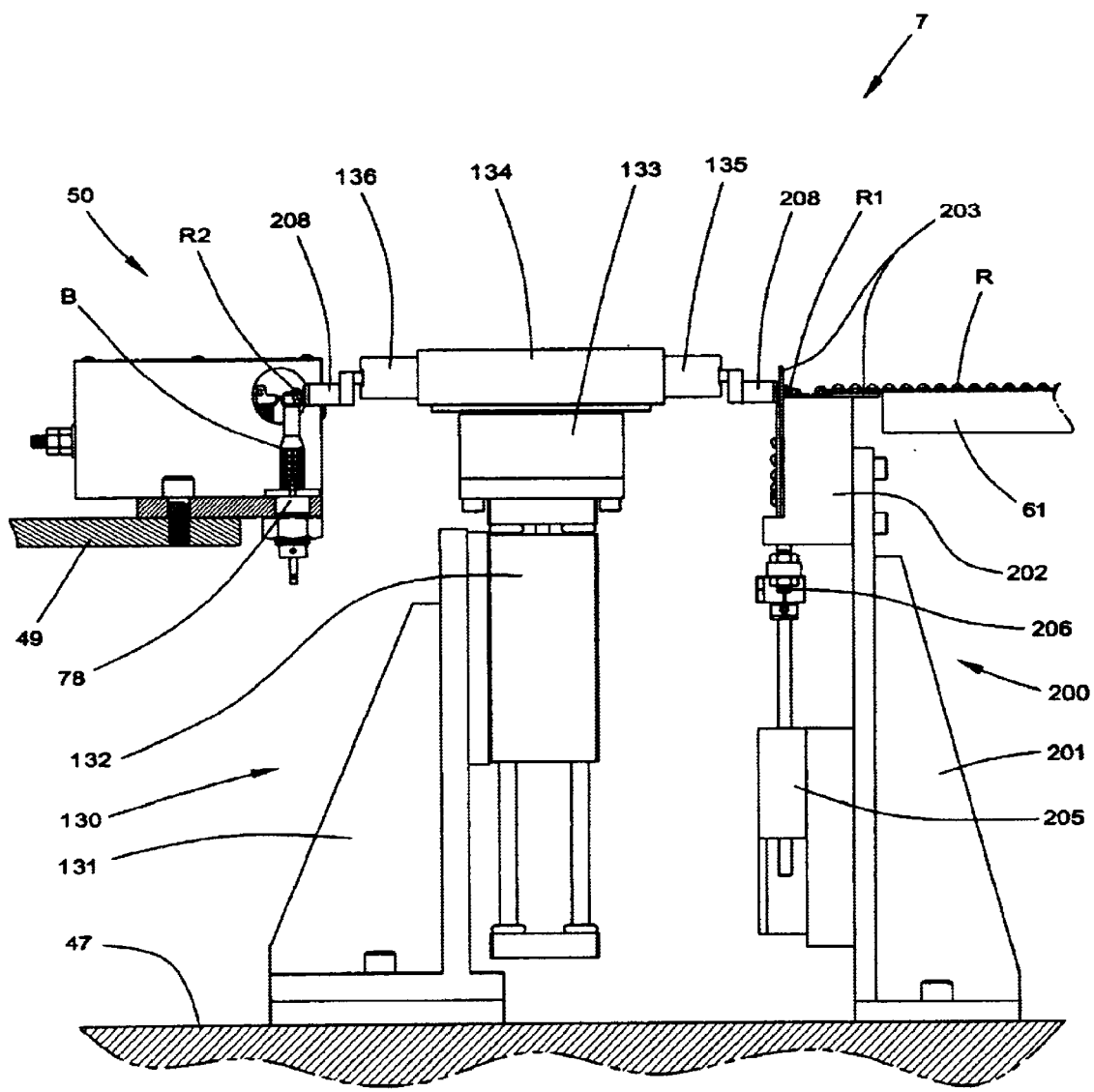
FIG. 26 is a partially cross-sectioned side view of Station Seven shown in FIG. 22 with the pick-and-place mechanism in the "down" position and the isolator slide in the "up" position.

Referring to FIGS. 22, 25 and 26, a pick-and-place unit 130 is mounted to the main base 47 at Station Seven 7 between the rotor isolator 200 and the dial plate 49. The pick-and place unit 130 consists of a welded steel frame 131 to which is mounted an air-driven slide 132 to provide up and down motion of about three inches. Mounted on top of the slide 132 is an air-driven, 180° rotary actuator 133 to which is attached a gripper mounting plate 134 with four air-driven, parallel grippers. Each of the four grippers is equipped with a pair of fingers shaped for clamping the button of the rotor.

Referring to FIGS. 22, 25 and 26, a pick-and-place unit 130 is mounted to the main base 47 at Station Seven 7 between the rotor isolator 200 and the dial plate 49. The pick-and-place unit 130 at Station Seven 7 is identical to the pick-and-place 130 at Station One 1 and Station Three 3 described above except for the gripper fingers 208 which are shaped to grip rotors R instead of bodies or drive shafts.

At Station Seven 7, rotors are inserted into the bodies as follows:

Step 1: The isolator slide 205 extends to its "up" position, shown in FIG. 26, causing the studs 206 to engage, from below, the two rotors R1 at the sharp turns 204 in the tracks 203 of the isolator 200. The two rotors R1 are lifted in the isolator 200 by the studs 206. The rotors R1 are guided by the tracks 203 extending upward from the isolator block 202. Simultaneously, the pick-and-place 130 lowers to its "down" position where two rotors R2 already held by the closed grippers 136 are placed into a pair of bodies B in the fixture 50 on the dial plate 49. This downward motion also places the open grippers 135 in position to grip the two rotors R1 lifted by the isolator 200 at the end of the tracks 203.

Step 2: Sensors verify these motions so that immediately upon completion, the two grippers 135 close, gripping the two rotors R1 in the isolator 200, while the two grippers 136 open, releasing two rotors R2 in the fixture 50.

Step 3: The pick-and-place 130 lifts, removing the two rotors R1 from the isolator 200 and leaving two rotors R2 in the fixture 50. At the same time, the isolator slide 205 retracts to its "down" position shown in FIG. 25, lowering the studs 206, which creates an open space at the sharp turns 204 in the isolator tracks 203. The vibratory in-line feeder 61 advances the rotors R forward, filling the two open spaces with the next rotor R in each track 203.

Step 4: When the pick-and-place 130 reaches the "up" position, the rotary actuator 133 rotates 180° transferring the rotors R1 from a position directly above the isolator 200 to a position directly above the bodies B in a fixture 50 on the dial plate 49. Simultaneously, the dial plate 49 indexes, moving the fixtures 50 one position to the next station.

Figure 27:
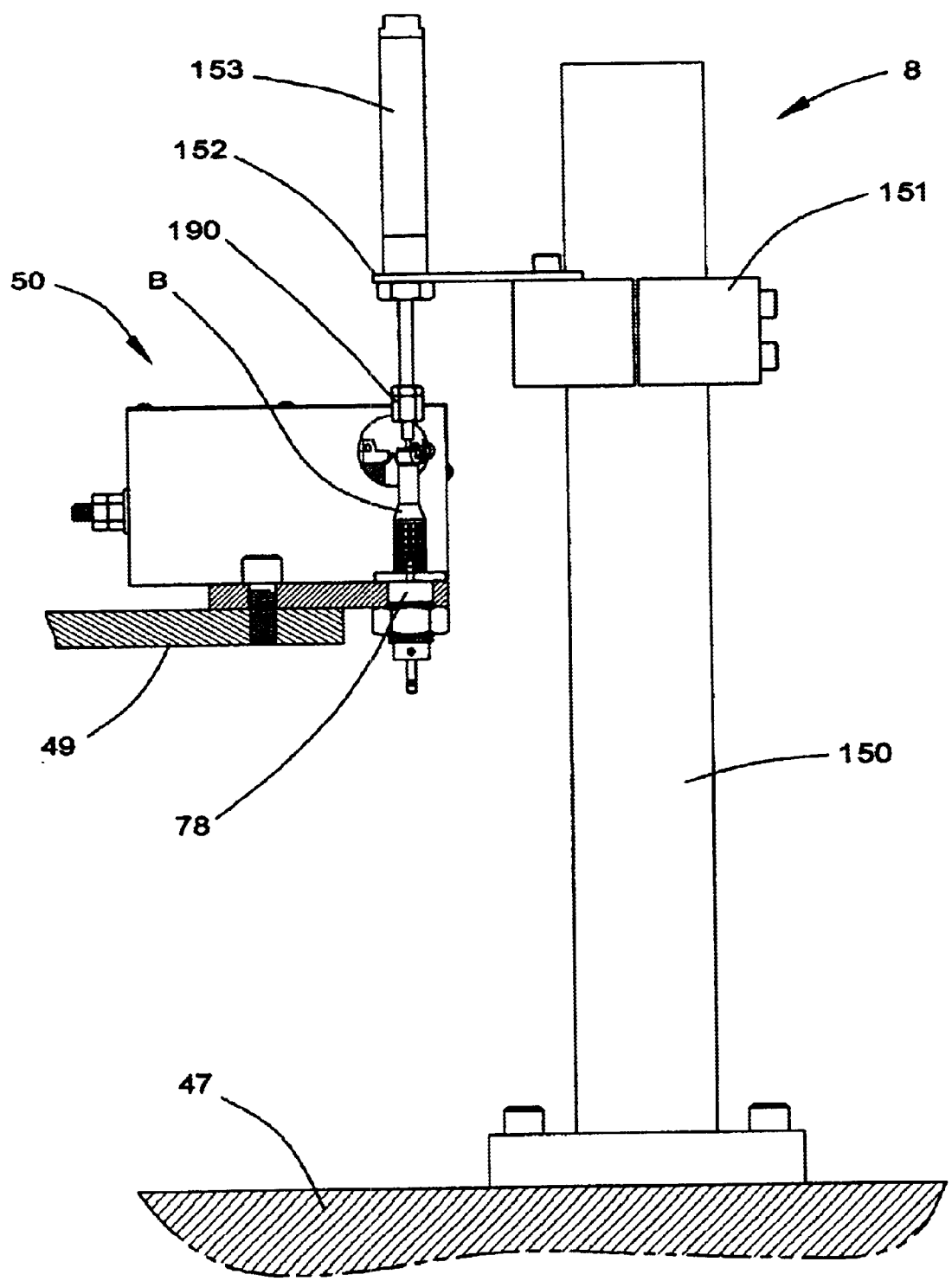
FIG. 27 is a partially cross-sectioned side view of Station Eight shown in FIG. 12.

At Station Eight 8, the rotors R are seated in the bearings of the angle body B. Referring to FIGS. 12 and 27, Station Eight 8 is identical in construction and operation to Station Five 5 described above. The operation at Station Eight 8 occurs as follows:

Step 1: The air cylinders 153 extend downward so that the tip 190 of each air cylinder rod makes contact with the rotor R in the fixture 50. The cylinders 153 apply downward pressure to the rotors R ensuring that they are properly seated in the bearings of the angle body B.

Step 2: No action occurs.

Step 3: The air cylinders 153 retract.

Step 4: The dial plate 49 indexes moving the fixtures 50 one position to the next station.

Figure 28:
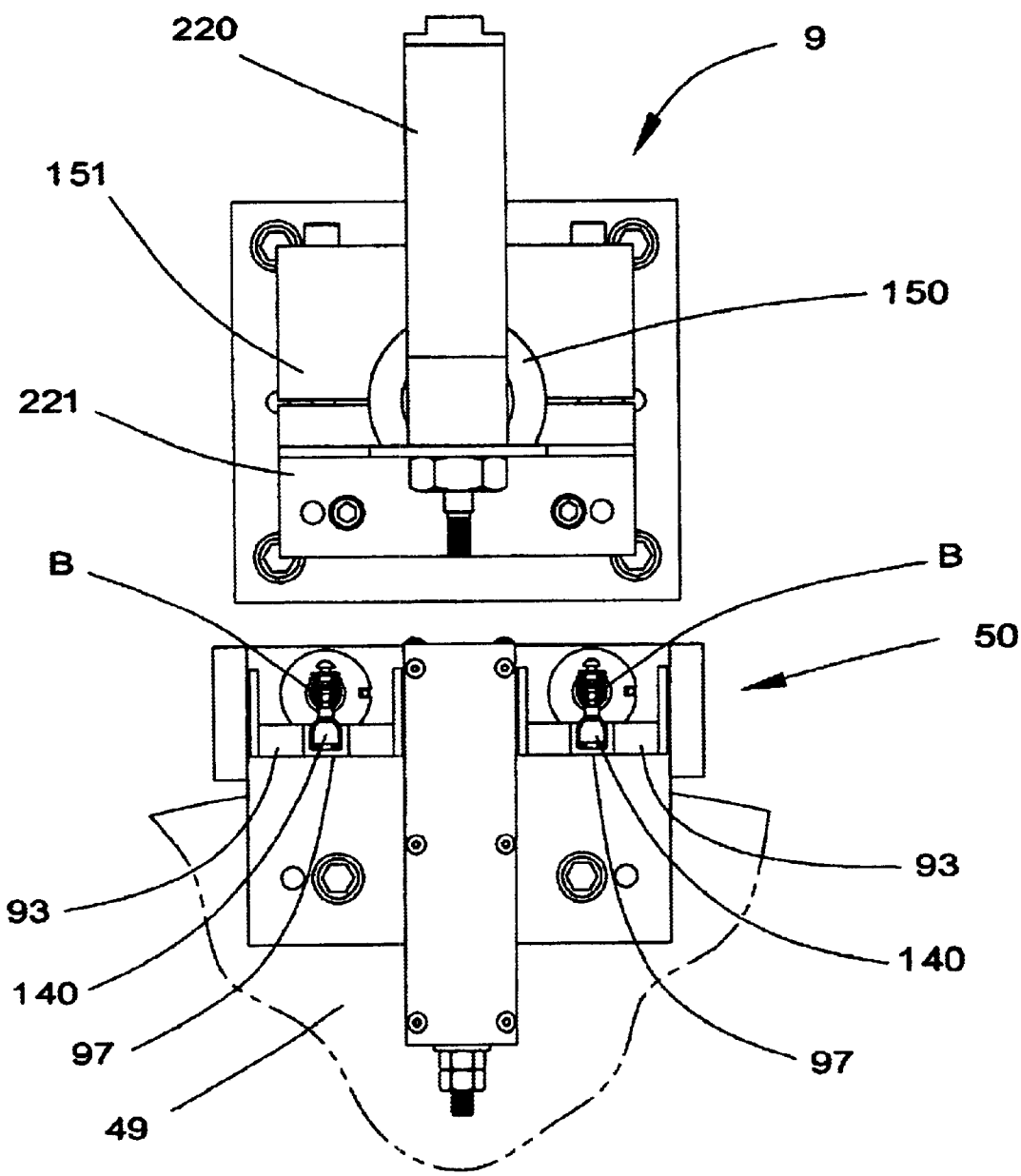
FIG. 28 is a plan view of Station Nine of the preferred embodiment.
Figure 29:
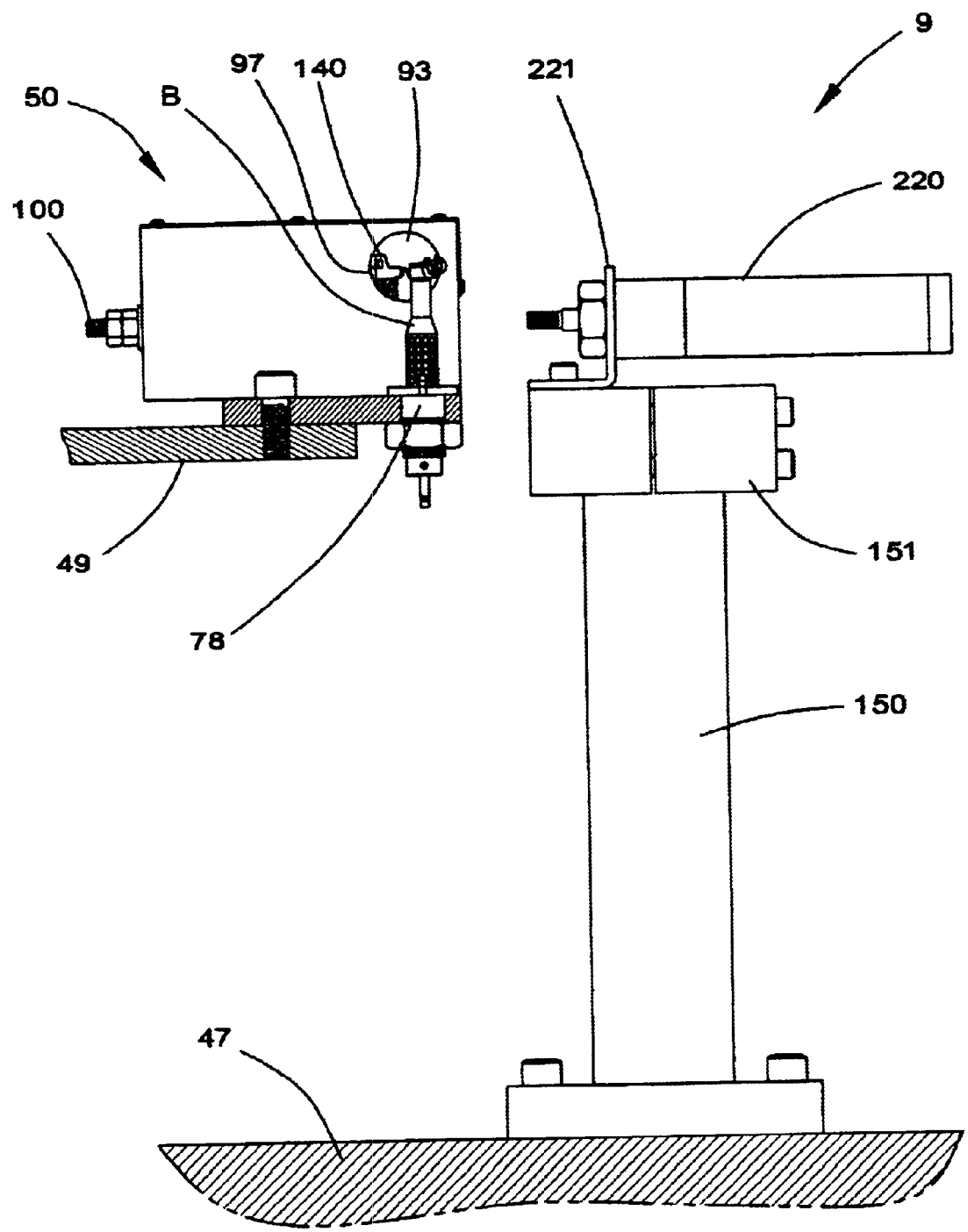
FIG. 29 is a partially cross-sectioned side view of Station Nine shown in FIG. 28 with the air cylinder retracted and the fixture in the "open" position.
Figure 30:
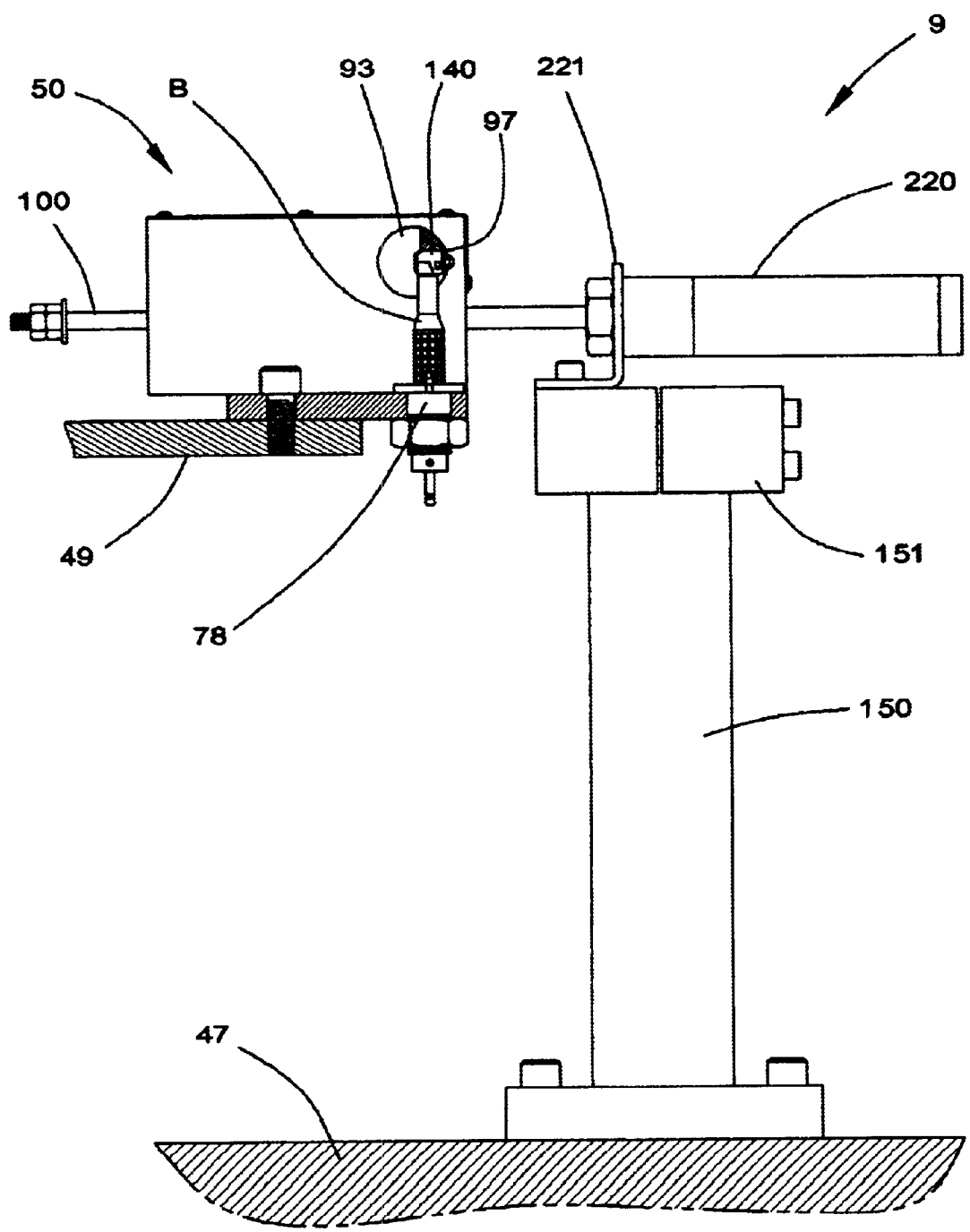
FIG. 30 is a partially cross-sectioned side view of Station Nine shown in FIG. 28 with the air cylinder extended and the fixture in the "closed" position.

At Station Nine 9, the angle body is snapped closed. Referring to FIGS. 28 thru 30, a support post 150 is mounted to the main base 47 at Station Nine 9. A clamp block 151 is attached to the support post 150. The support post 150 and clamp block 151 are preferably identical to those described above making the stations modular so that they may be easily interchanged. An angle plate 221 is attached to the clamp block 151. An air cylinder 220 is mounted to the angle plate 221. The air cylinder 220 is positioned to extend horizontally toward the center of the dial 49 in alignment with the push rod 100. The operation occurs at Station Nine 9 as follows:

Step 1: As described above, the closures 140 rest in the recesses 97, of the shaft 93 as shown in FIG. 29. The air cylinder 220 extends as shown in FIG. 30, pushing the push rod 100, which causes the shaft 93 to rotate. As the shaft 93 rotates, the closures 140 are bent over until both bodies B are snapped closed in the fixture 50.

Step 2: No action occurs.

Step 3: The air cylinder 220 retracts allowing the tension of the spring 105, shown in FIG. 3, to return the push rod 100 and the shaft 93 to their original positions.

Step 4: The dial plate 49 indexes, moving the fixtures 50 one position to the next station.

Station Ten 10 is not used in the preferred embodiment. Since only thirteen stations are required in this embodiment, Station Ten 10 is intended to be used in alternative embodiments some of which are described below.

Figure 31:
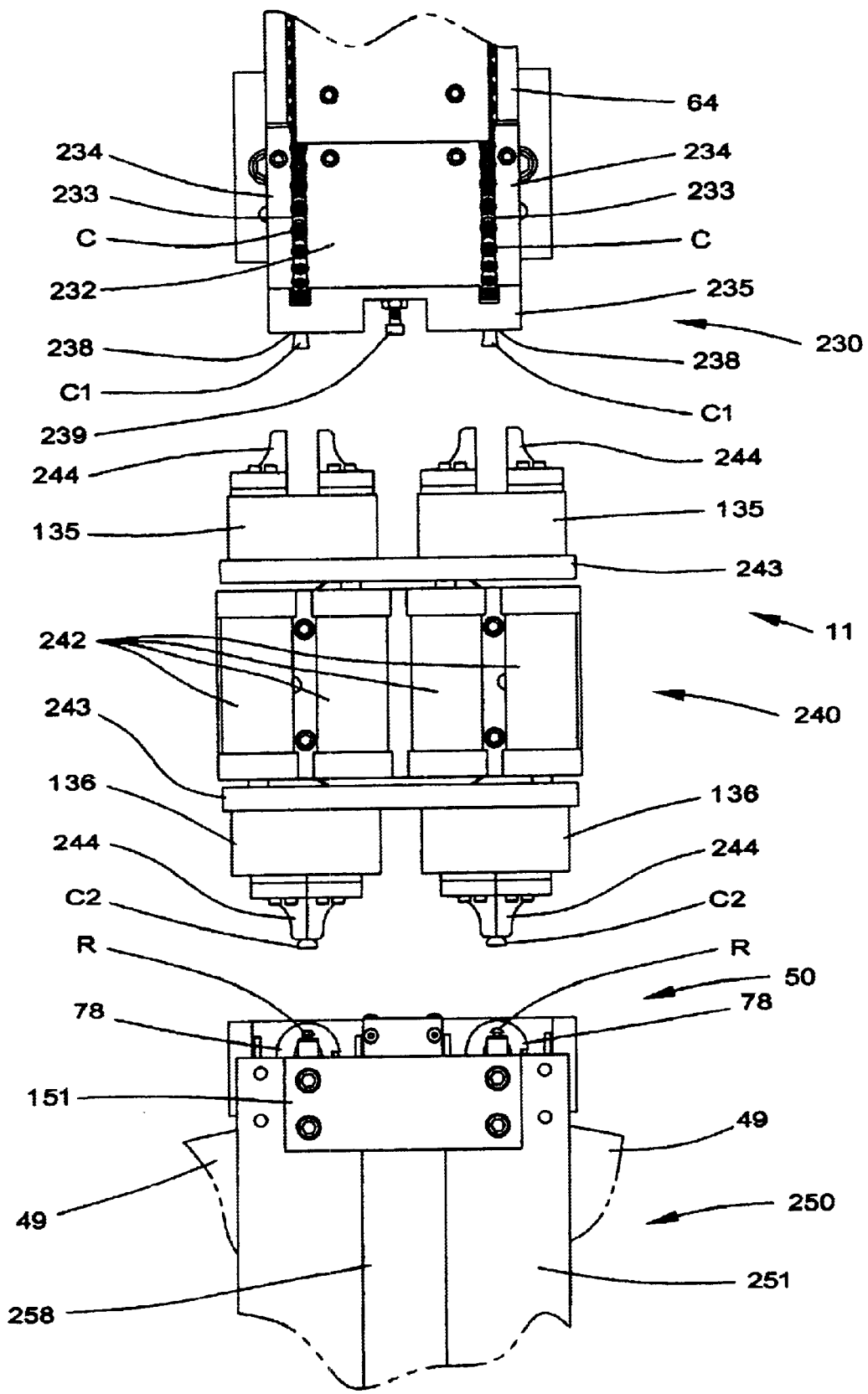
FIG. 31 is a plan view of Station Eleven of the preferred embodiment.
Figure 32:
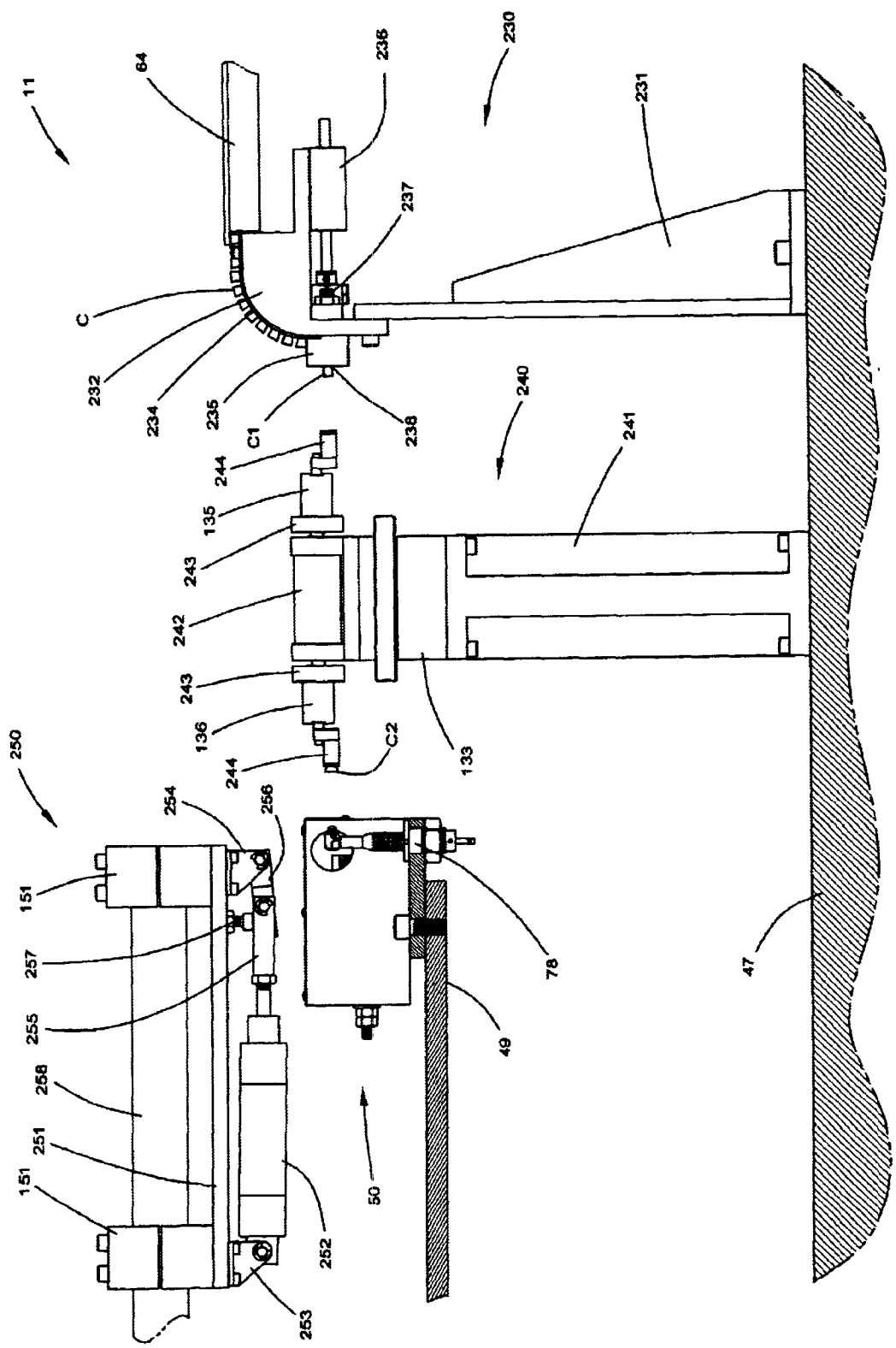
FIG. 32 is a partially cross-sectioned side view of Station Eleven shown in FIG. 31 with the pick-and-place in its retracted position and the isolator in its extended position.
Figure 33:
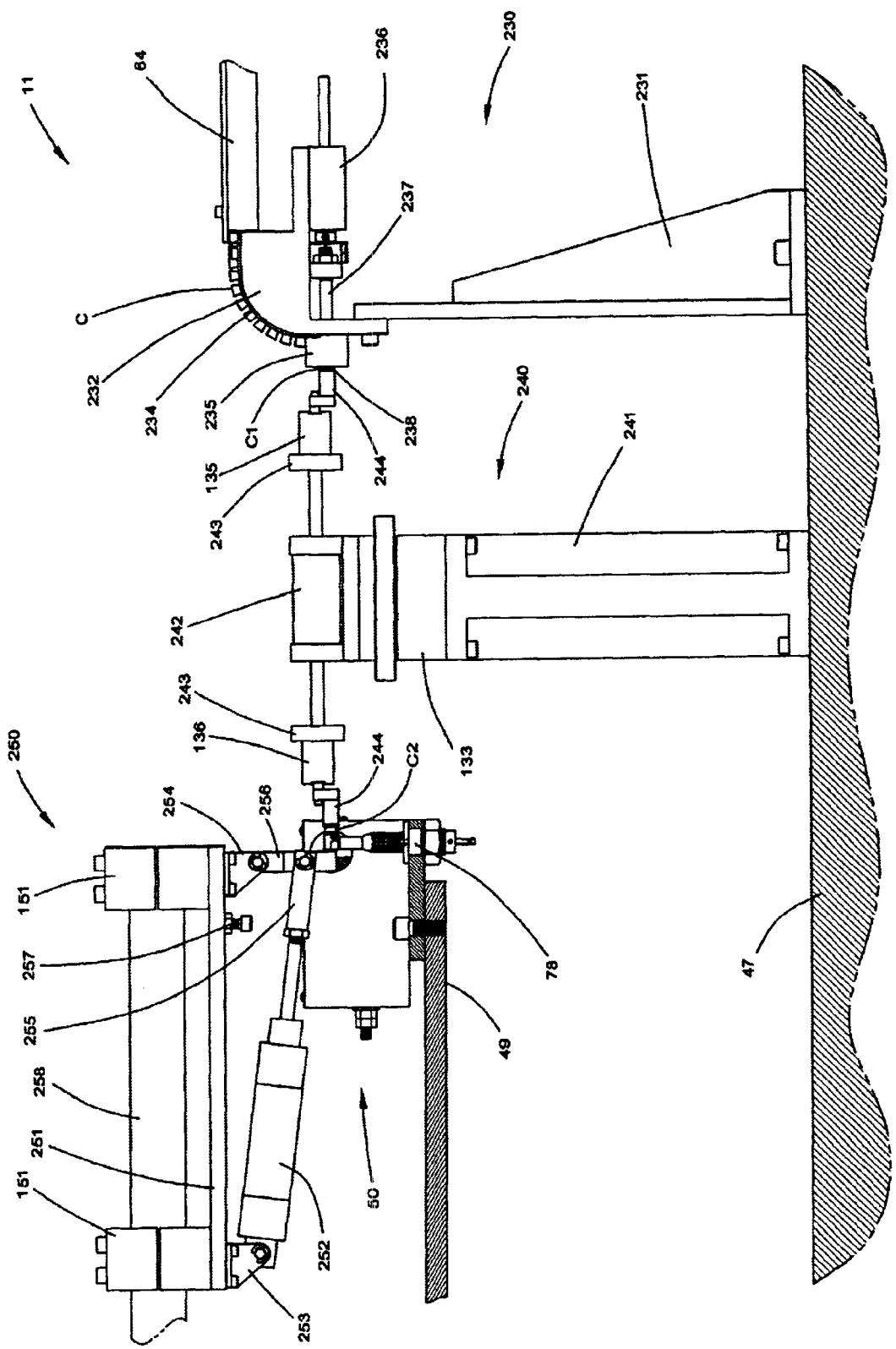
FIG. 33 is a partially cross-sectioned side view of Station Eleven shown in FIG. 31 with the pick-and-place in its extended position and the isolator in its retracted position.

At Station Eleven 11, the prophy cup is installed on the angle. Referring to FIG. 2, a feed module 45 feeds prophy cups to Station Eleven 11. This feed module 45 consists of a steel base 62 similar to the main base 47 described above but sized for mounting a vibratory feeder bowl 63 and an in-line vibratory feeder 64. Both the feeder bowl 63 and the in-line feeder 64 are dual-line feeders so the prophy cups can be fed in pairs to the station 11. In the feeder bowl 63, prophy cups are oriented, diameter-to-diameter, axis vertical, large diameter down, and fed to the in-line feeder 64 as shown in FIGS. 31 thru 33. The in-line feeder 64 serves as both a feeder and a magazine to the prophy cup isolator 230.

Referring to FIGS. 31 thru 33, the prophy cup isolator 230 includes a welded steel frame 231 mounted at Station Eleven 11. A rotator block 232 containing a pair of grooves 233 for receiving prophy cups C from the in-line feeder 64 is attached at the top of the frame 231. The in-line feeder 64 feeds cups C into the two grooves 233 of the rotator block 232. The grooves 233 curve downward reorienting the cups C, axis horizontal, spaced apart a distance equal to the distance between the mounting posts 78 in the fixture 50. Containment rails 234 prevent the cups C from falling out of the grooves 233. The cup isolator block 235 is mounted to the rotator block 232. Also mounted to the rotator block 232 is an air-driven slide 236 to which a pair of studs 237 is attached in axial alignment with the first pair of cups C1 at the end of the grooves 233. Two holes 238 provide a passage for each stud 237 through both the rotator block 232 and the isolator block 235 at the end of the grooves 233. A screw 239 is located in a threaded hole in the isolator block 235. The end of this screw 239 makes contact with the air driven slide 236 and is used to adjust the stroke of the slide 236 and, consequently, how far the cups C1 extend from the isolator block 235.

A pick-and-place unit 240 is mounted to the main base 47 at Station Eleven 11 between the cup isolator 230 and the dial plate 49. The pick-and place unit 240 consists of a steel frame 241 to which is mounted an air-driven, 180° rotary actuator 133. On top of the rotary actuator 133, two pairs of air cylinders 242 are mounted to extend horizontally in opposite directions. Attached to each pair of cylinders 242 is a gripper mounting plate 243 with two pairs of air-driven, parallel grippers 135 and 136. Each of the four grippers 135 and 136 is equipped with a pair of fingers 244 shaped for clamping a prophy cup C.

A head support mechanism 250 is mounted directly above the fixture 50 at Station Eleven 11. The head support mechanism 250 consists of a base plate 251 located in a generally horizontal position directly above the fixture 50 at Station Eleven 11. A pair of air cylinders 252 is mounted side-by-side to the lower side of the base plate 251. The air cylinders 252 are mounted to the base plate 251 by a first pair of pivot brackets 253 and are each equipped with a clevis 255. Both the pivot brackets 253 and the devises 255 are commonly purchased with the air cylinders 252. Each clevis 255 is attached to a pivot arm 256 that is mounted by a second pair of pivot brackets 254 to the base plate 251. A screw 257 is included in the base plate 251 to prevent each pivot arm 256 from aligning with its air cylinder 252, a position where the air cylinders 252 may fail to actuate.

The head support mechanism 250 is mounted to a pair of clamp blocks 151 directly above the fixture 50 at Station Eleven 11. A tubular frame 258, preferably made from steel pipe, extends horizontally from the stationary center post 68 described above and shown in FIG. 2. The clamp blocks 151, preferably the same as those described above, are used to attach the head support mechanism 250 to the tubular frame 258.

Consistent with the modular concept, the rotary actuator 133 and the grippers 135 and 136 are preferably identical to those described above. This arrangement simplifies the design and the manufacture of the components and allows interchangeability of components between stations.

At Station Eleven prophy cups are installed as follows:

Step 1: The isolator slide 236 extends causing the studs 237 to shove the first pair of prophy cups C1 through the pair of holes 238 in the isolator block 232. The cups C1 emerge from the holes 238 in the isolator block 232 extending about ¼ inch from the surface of the block 232. The holes 238 are sized to provide interference fit with the large diameters of the cups C1. This interference fit holds the cups C1 in place for the gripper fingers 244. Simultaneously, the two pairs of air cylinders 242 of the pick-and-place 240 extend shoving the two prophy cups C2, already held by the closed grippers 136, onto the rotors R of the two angles in the fixture 50. This motion also places the open grippers 135 in position to grip the two cups C1 extending from the isolator block 232.

Step 2: Sensors verify these motions so that immediately upon completion, the two grippers 135 near the isolator 230 close, gripping the two cups C1 extending from the isolator block 232. At the same time the two grippers 136 at the fixture 50 open, releasing two cups C2 that are now attached to the rotor R.

Step 3: The cylinders 242 of the pick-and-place 240 retract, removing the two cups C1 from the isolator block 232 and leaving the two cups C2 attached to the rotor R in the fixture 50. At the same time, the isolator slide 236 retracts the studs 237, which creates an open space at the end of the isolator grooves 233. The vibratory in-line feeder 64 pushes the cups C forward, filling the two open spaces with the next prophy cup C in each groove 233.

Step 4: When the pick-and-place cylinders 242 are retracted, the rotary actuator 133 rotates 180° transferring the cups C1 from a position near the prophy cup isolator 230 to a position directly in line with the rotors R in the fixture 50. Simultaneously, the dial plate 49 indexes, moving the fixtures 50 one position to the next station.

At Station Twelve, the assembled angles are inspected to verify the presence of the drive shafts, rotors, and cups.

Figure 34:
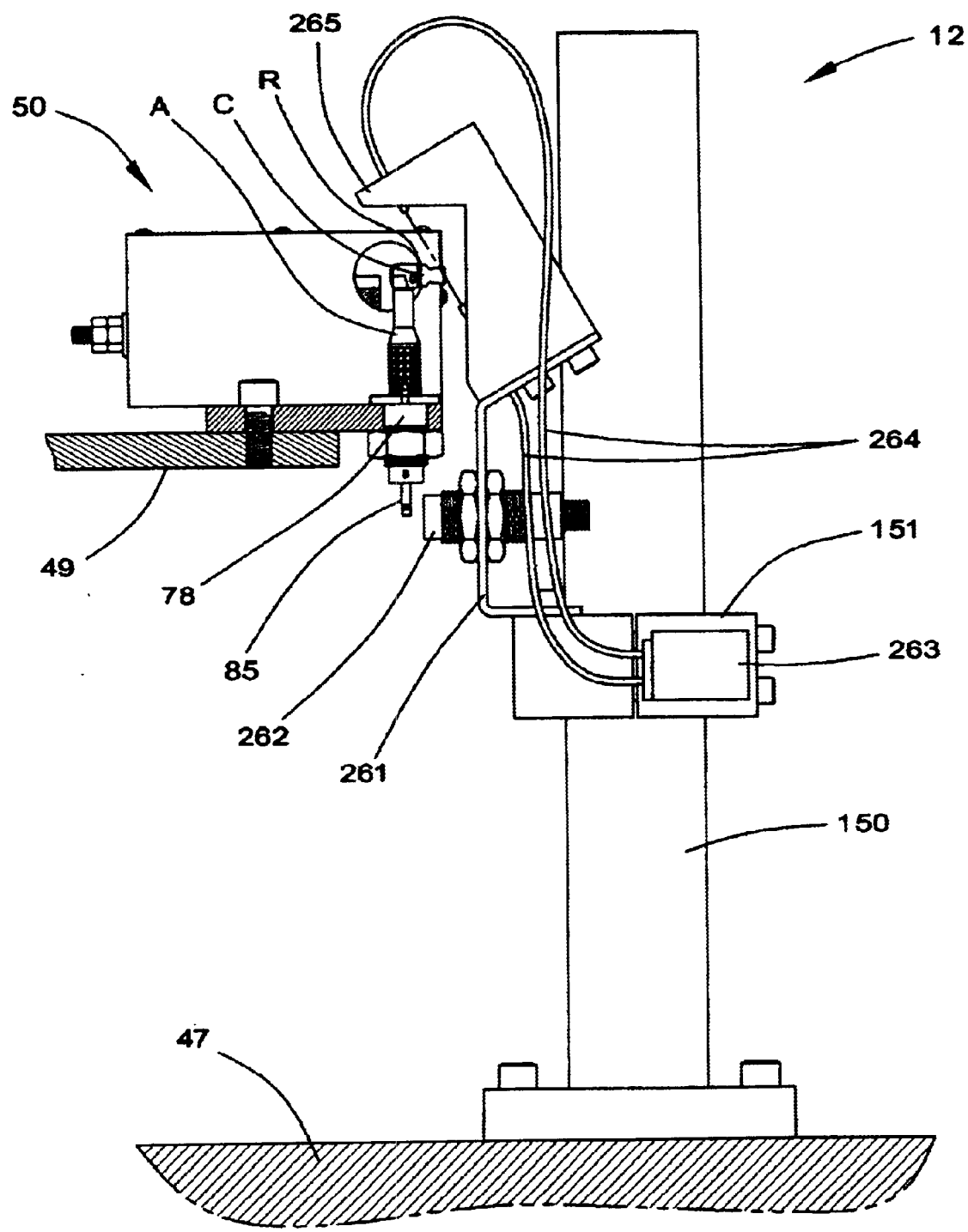
FIG. 34 is a partially cross-sectioned side view of Station Twelve of the preferred embodiment.

Station Twelve 12, shown in FIG. 34, consists of a station post 150 to which a clamp block 151 is attached. A sensor-mounting bracket 261 is attached to the clamp block 151. The sensor-mounting bracket 261 supports two pairs of sensors. The first pair of sensors 262 detects the presence of the prophy angle drive shaft. These sensors 262 are preferably non-contact, solid state, inductive proximity sensors but may be any type of sensors or switches that will indicate the presence of the pins 85. In the preferred embodiment, the two sensors 262 are mounted just below and at the perimeter of the dial plate 49 in a one-to-one relationship with the mounting posts 78.

The presence of drive shafts is determined by detecting the pins 85 extending downward from the mounting posts 78 below the dial plate 49. The pair of inductive proximity sensors 262 is mounted to detect the pins 85. If one of the sensors 262 does not detect its corresponding pin 85, the drive shaft on that mounting post 78 is not present in that angle A, and the angle A will be rejected at Station Thirteen 13 described below.

The second pair of sensors 263 detects the presence of the prophy cup C. These sensors 263 are preferably non-contact, solid state, photoelectric sensors using fiber optic cables 264 to direct the light beam at the prophy cup C. Again, any type of sensor or switch capable of indicating the presence of the prophy cup C may be used. In the preferred embodiment, the sensors 263 are fastened to the opposite sides of the clamp block 151 as shown in FIG. 34. A pair of holders 265 is attached to the sensor-mounting bracket 261 and directs the light beams from the photoelectric sensors 263 at the prophy cups C in the fixture 50.

Both prophy cups C and rotors R are detected by the photoelectric sensors 263. Fiber optic cables 264 from each sensor 263 are mounted in the holders 265 such that the beams of light carried by the cables 264 are broken by the presence of the prophy cups C in the fixture 50. If the light beam of either sensor 263 is not interrupted, the prophy cup C corresponding to that sensor 263 is not present. Either the angle A was assembled without a cup C, or the angle A was assembled without a rotor R and, therefore, the cup C could not be attached. In either case, the angle A will be rejected at Station Thirteen 13.

Figure 35:
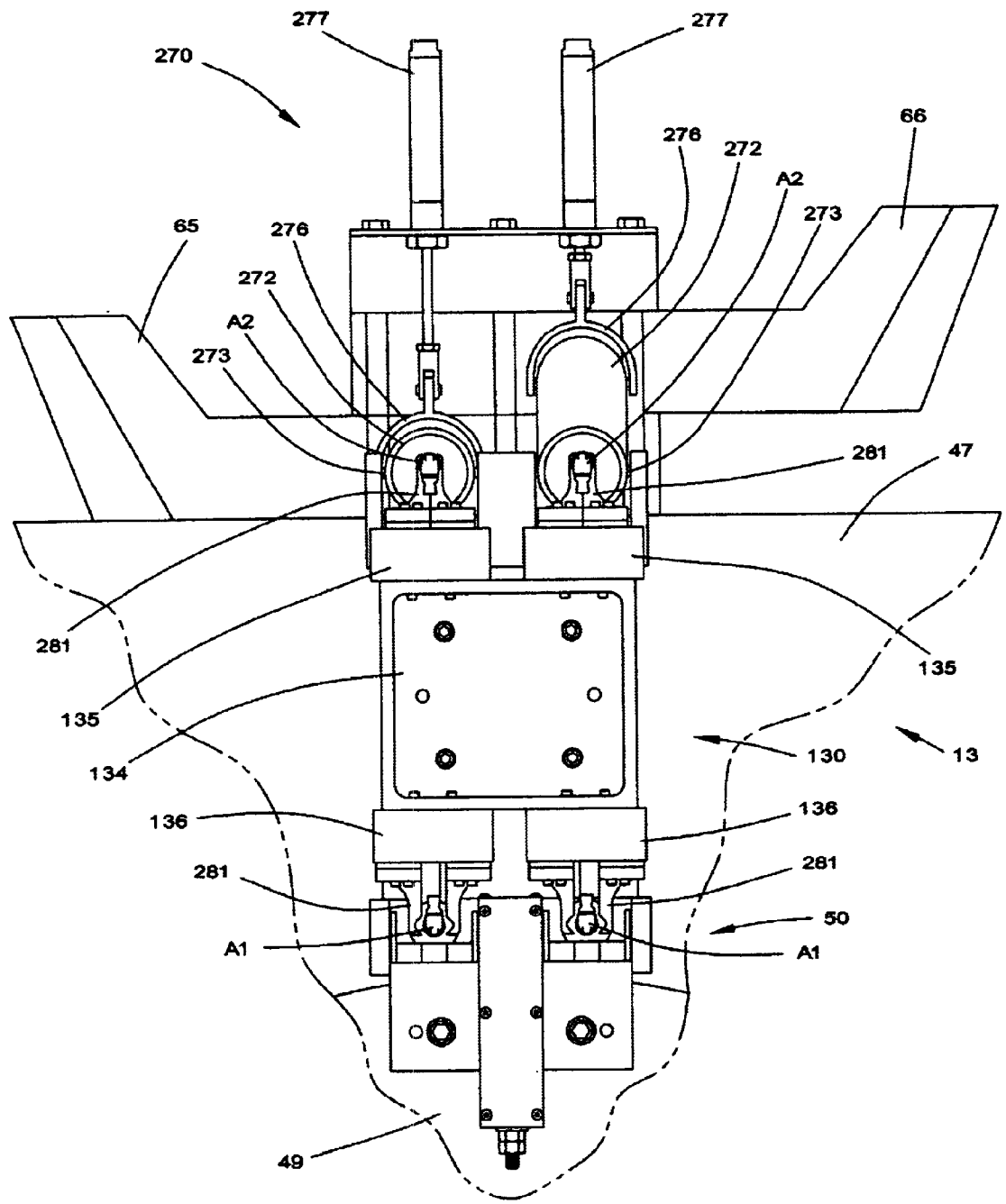
FIG. 35 is a plan view of Station Thirteen of the preferred embodiment.
Figure 36:
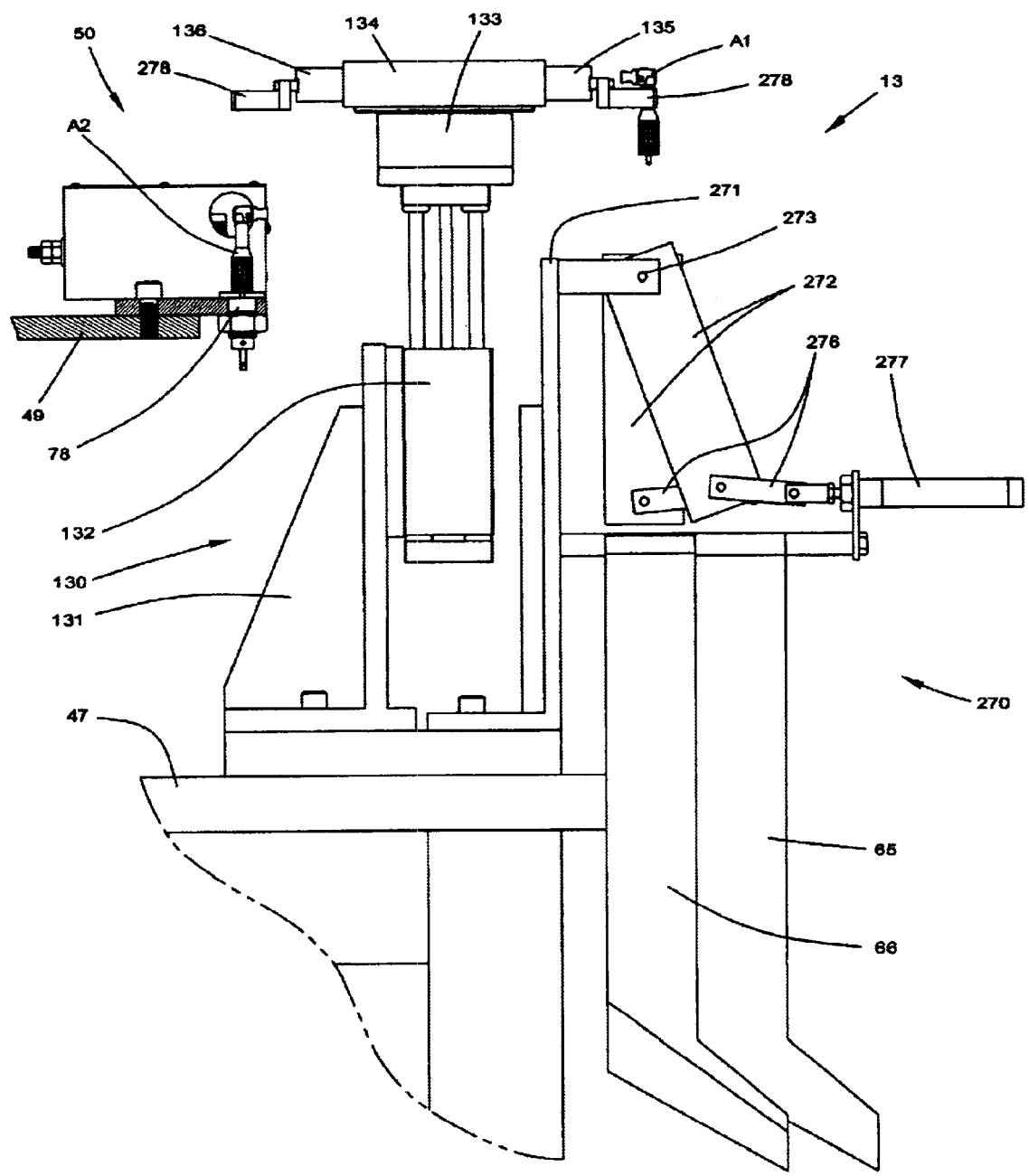
FIG. 36 is a partially cross-sectioned side view of Station Thirteen shown in FIG. 35 with the pick-and-place in the "up" position with one tube in the "accept" position and one tube in the "reject" position.
Figure 37:
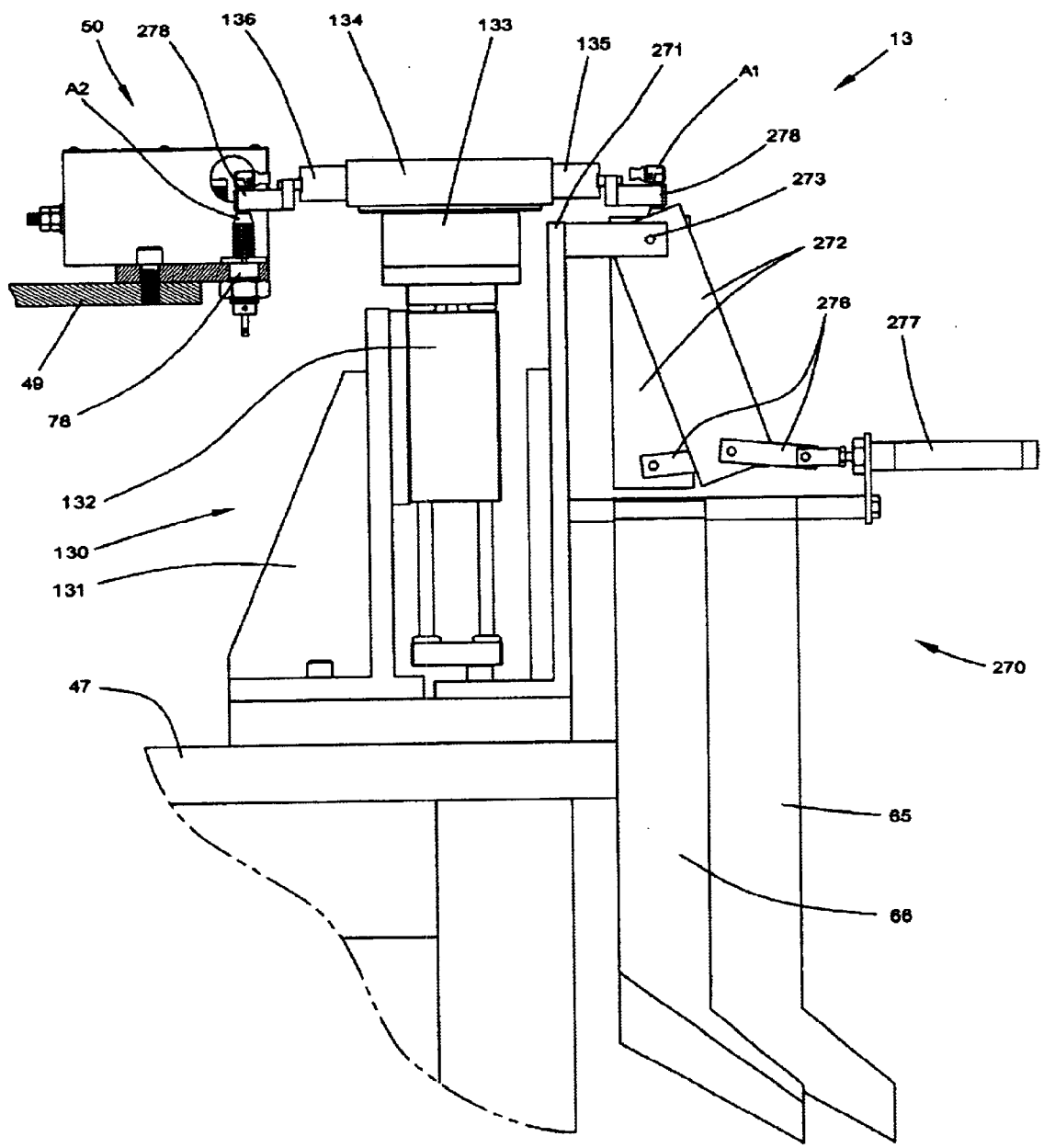
FIG. 37 is a partially cross-sectioned side view of Station Thirteen shown in FIG. 35 with the pick-and-place in the "down" position with one tube in the "accept" position and one tube in the "reject" position.

The assembled angles A are removed from the fixture 50 and are either accepted or rejected by the diverter mechanism 270 at Station Thirteen 13 shown in FIGS. 35 thru 37. The diverter mechanism 270 consists of a steel frame 271 to which is mounted a pair of tubes 272 hanging by pins 273 that allow the tubes 272 to swing back and forth. Below the tubes 272, a first chute 66 for receiving accepted angles extends downward at a 45° incline from the frame 271 along the main base 47. Also below the tubes 272, a second chute 65, for receiving rejected angles, extends downward at a 45° incline from the frame 271 along the main base 47 in the direction opposite the first chute 66. A yoke 276 attaches a horizontally mounted air cylinder 277 to the bottom of each tube 272 such that when either air cylinder 277 is extended, the lower end of the tube 272 is positioned over the "rejects" chute 65, and when retracted, over the "accepts" chute 66.

A pick-and-place unit 130 is mounted to the main base 47 at Station Thirteen 13 between the dial plate 49 and the diverter mechanism 270. The pick-and place unit 130 consists of a welded steel frame 280 to which is mounted an air-driven slide 131 to provide up and down motion of about three inches. Mounted on top of the slide 131 is an air-driven, 180° rotary actuator 133 to which is attached a gripper mounting plate 134 with four air-driven, parallel grippers 135 and 136. Each of the four grippers is equipped with a pair of fingers shaped for clamping the neck of an angle body.

Referring to FIGS. 35 thru 37, assembled angles A are removed from the fixture 50 as follows:

Step 1: The pick-and-place 130 lowers to its "down" position where two angles A1 already held by the closed grippers 135 are positioned in the tops of the two diverter tubes 272. This downward motion also places the open grippers 136 in position to grip the two angles A2 in the fixture 50.

Step 2: Sensors verify these motions so that immediately upon completion, the two grippers 136 in the fixture 50 close, gripping the angles A2 in the fixture 50, while the two grippers 135 at the diverter 270 open, dropping the two angles A1 into the diverter tubes 272. The angles A1 fall through the tubes 272 and, if accepted, slide down the "accepts" chute 66 to the bagging unit feed conveyor 23 shown in FIGS. 1 and 2. If rejected, the angles slide down the "rejects" chute 65 and fall into a container 22 below.

Step 3: The pick-and-place 130 lifts, removing the two angles A2 from the fixture 50 as the other two angles A1 fall through the diverter tubes 272.

Step 4: When the pick-and-place 130 reaches the "up" position, the rotary actuator 133 rotates 180° transferring the angles A2 from a position directly above the fixture 50 to a position directly above the tubes 272 of the diverter mechanism 270. Simultaneously, the dial plate 49 indexes moving the fixtures 50 one position to the next station.

At Station Fourteen, the fixture is reset.

Figure 38:
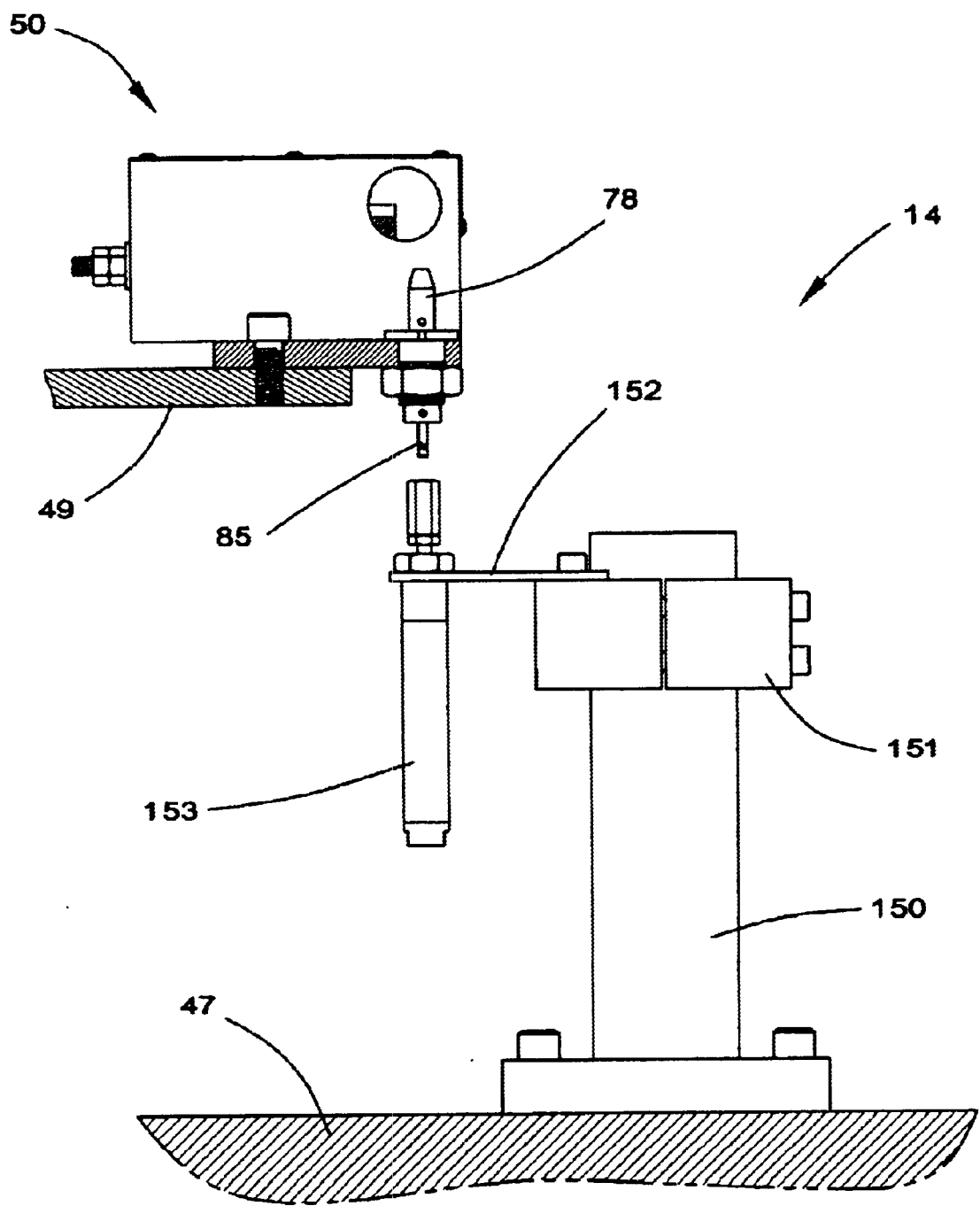
FIG. 38 is a partially cross-sectioned side view of Station Fourteen of the preferred embodiment.

Referring to FIG. 38, Station Fourteen 14 consists of a station post 150 to which is mounted a clamp block 151 and a cylinder mounting plate 152 in the same manner as Station Two described above. A pair of air cylinders 153 is mounted below the dial plate 49 in axial alignment with the mounting posts 78.

Step 1: The air cylinders 153 extend upward shoving the pins 85 back into the mounting posts 78.

Step 2: No action occurs.

Step 3: The air cylinders 153 retract.

Step 4: The dial plate 49 indexes, moving the fixtures 50 one position to the next station.

Stations Fifteen 15 and Sixteen 16, shown in FIG. 2, are not used in this embodiment. These stations, along with Station Ten 10 are intended for alternate embodiments in which additional operations are required. In one alternative embodiment, a prophy angle consisting of five components is assembled. In this embodiment, any of these additional stations 10, 15, and 16 may be used as an additional assembly station, an additional lubrication station, or an additional inspection station.

The assembly unit 17 is preferably controlled by a programmable logic controller (PLC) located in the operator control panel 67 mounted to the body feed module base 51. The timing of all operations of the assembly unit 17 are preferably controlled logically by the PLC instead of mechanically. Logical timing involves sensing each machine operation and proceeding with the next operation in a step-by-step manner as described above only when all of the operations of the previous step have been sensed confirmed by the PLC. Therefore, the assembly unit 17 is preferably equipped with sensors to confirm the completion of each operation. These sensors are preferably solid-state such as Hall effect, proximity, or photoelectric types that are typically optional equipment on most air cylinders, slides, and rotary actuators as is commonly known in the art.

Figure 39:
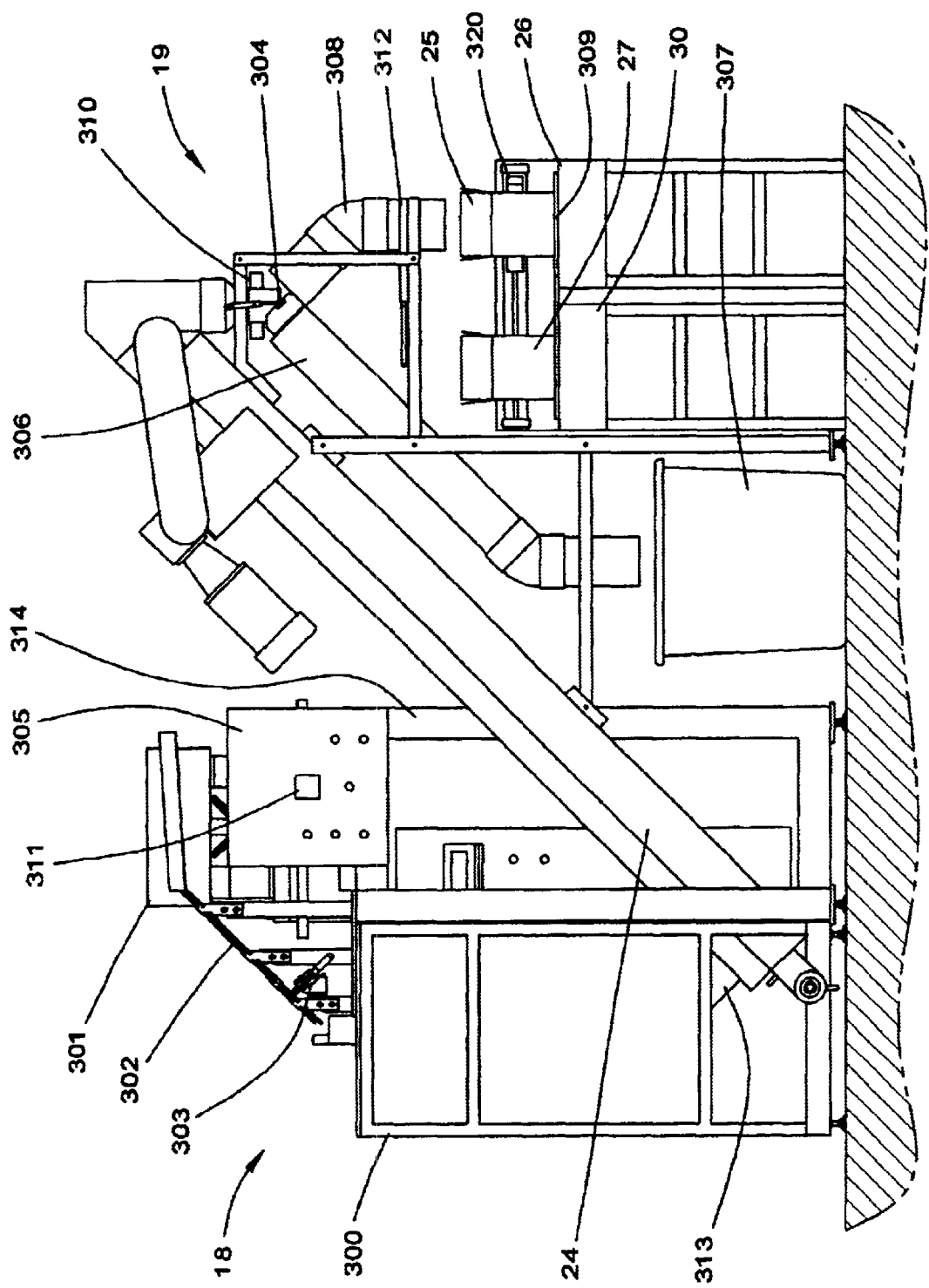
FIG. 39 is an elevation view of the bagging and batch-counting units of the preferred embodiment.

The accepted angles from the assembly unit 17 are carried from Station Thirteen 13 by a first belt conveyor 23 to the bagging unit 18 as shown in FIG. 1. Referring to FIG. 39, the bagging unit 18 preferably includes a vertical form-fill-and-seal bagging machine 300 that is readily available and commonly known to those skilled in the art. The bagging unit 18 also includes a vibratory feeder bowl 301, and a gravity track magazine 302 equipped with an escapement mechanism 303.

A base 314 supports the vibratory feeder bowl 301. This base 314 is preferably constructed as a steel weldment similar to the bases described above but sized to position the feeder bowl 301 above the bagging machine 300. The base 314 is preferably attached to the bagging machine 300 to stabilize the feeder bowl 301 and maintain its precise position relative to the bagging machine 300.

The vibratory feeder bowl 301 receives the assembled angles from the belt conveyor 23, orients the angles to be accepted by the bagging machine 300, and feeds them to a gravity track magazine 302 located directly above the bagging machine 300. The feeder bowl 301 also provides accumulation of angles and, therefore, serves as a buffer between the assembly unit 17 and the bagging machine 300 to ensure an uninterrupted supply of angles to the bagging machine 300. Since it is equipped with its own feeder bowl 301, the bagging unit 18 does not have to be integrated with the assembly machine 17, but may be operated independently as further described below. This reduces overall downtime by allowing the bagging unit 18 to continue to operate in the event the assembly unit 17 is not in operation, say due to maintenance or repair, and vice versa.

The escapement mechanism 303, which is triggered by the bagging machine 300 to ensure proper timing, is located near the end of the magazine 302, releasing one angle at a time into the bagging machine 300. The angles fall, by gravity, preferably head first, through the bagging machine 300 where they are sealed in individual bags.

The individually bagged angles drop by gravity from the bagging machine 300 and slide down a chute 313 onto a second belt conveyor 24 that carries them to the batch-counting unit 19. The chute 313 is removable so that the bagging unit 18 may be operated independent of the rest of the machine as described below.

The batch-counting unit 19 includes a diverting mechanism 304 that accepts or rejects the bagged angles based on a signal from the bagging unit 18. This signal, indicating a malfunction in the bagging unit 18, activates the diverting mechanism 304 to reject improperly bagged angles. A switch is provided on the control panel 305 to allow the machine operator to manually override the diverting mechanism 304 so that angles may also be rejected at the operator's discretion. Bagged angles that have been rejected fall through the reject tube 306 into a container 307 for later review. Bagged angles that are not rejected by the diverting mechanism 304 fall through the fill tube 308 into an empty carton 25 at the fill position 309 located at the end of the first accumulating conveyor 26.

The batch-counting unit 19 also includes a sensor 310 to detect each bagged angle as it drops from the end of the belt conveyor 24. This sensor 310 is preferably optic, such as a light screen or an optical window, both of which are commonly known to those skilled in the art. A counter 311 mounted in the control panel 305 indicates both the actual batch count and a preset value that is input by the operator.

The batch-counting unit 19 is located directly above the first accumulating conveyor 26 that supplies it with empty cartons 25. The counter 311 counts bagged angles as they pass the sensor 310. When the count value reaches the preset value input by the operator, the counter 311 resets to zero and begins counting another batch of bagged angles. At the same time, a door 312 located near the lower end of the fill tube 308 closes creating a chamber within the fill tube 308. The fill tube 308 is sized to collect enough bagged angles, a dozen or so, to provide the time necessary to replace the full carton at the fill position 309 with an empty one 25.

An air cylinder 320 shoves the full carton from the fill position 309 on the first accumulating conveyor 26 to the second accumulating conveyor 30. The air cylinder 320 immediately retracts allowing an empty carton 25 to advance into the fill position 309. When the empty carton 25 reaches the fill position 309, the door 312 opens, dropping the bagged angles that have accumulated in the fill tube 308 while the previously filled carton 27 was being transferred.

Referring to FIG. 1, the second accumulating conveyor 30 carries full cartons 27 away from the batch-counting unit 19 to the carton-sealing unit 20. The carton-sealing unit 20, which is an item commonly known to those skilled in the art, is preferably integrated with the second accumulating conveyor 30 such that the full cartons 27 are closed and sealed by the carton-sealing unit 20 as they are carried by the accumulating conveyor 30.

From the carton-sealing unit 20, the accumulating conveyor 30 carries the sealed cartons 29 to an operator station 28 where the operator removes them. This same operator places empty cartons 25 onto the first accumulating conveyor 26 to continue the cycle. Sensors, preferably photoelectric, are mounted at various locations along the accumulating conveyors 26 and 30. These sensors are used for control purposes, as is common practice with the use of accumulating conveyors, to coordinate the operation of the batch-counting unit 19 and the carton-sealing unit 20 and to alert the operator in the event of a machine irregularity or malfunction.

In the preferred embodiment, the assembly unit 17, bagging unit 18, batch-counting unit 19, carton-sealing unit 20, both belt conveyors 23 and 24, and both accumulating conveyors 26 and 30 are integrated to operate as a single machine. However, the units are integrated in a way that permits independent operation of the individual units. As mentioned above, the assembly unit 17 is equipped with its own PLC to allow its operation independent of the rest of the machine. The bagging machine 18 is also equipped to operate independently. The batch-counting unit 19 is operated as an option to the bagging unit 18. And the carton-sealing unit 20 is operated as an option to the batch-counting unit 19.

The ability to operate individual units provides additional flexibility. For example, if the individually bagged angles are to be packaged in plastic bags instead of cartons 25, then reusable batch containers may be used instead of cartons 25 on the accumulating conveyors 26 and 30. The preferred embodiment provides for this situation by allowing the bagging and batch-counting units 18 and 19 to be operated without the carton-sealing unit 20. The accumulating conveyor 30 simply carries the reusable container full of bagged angles through the non-operational carton-sealing unit 20 to the operator station 28. At this point, the operator transfers the bagged angles from the reusable batch container to a plastic bag. Empty reusable batch containers are placed onto the first accumulating conveyor 26 the same as cartons 25 to repeat the cycle.

While a preferred automated assembly and packaging machine has been described in detail, various modifications, alterations, and changes may be made without departing from the spirit and scope of the present invention as defined in the appended claims.

What is claimed is:

1. A system for making dental prophylaxis angles, the system comprising: a plurality of mounting posts, each adapted to support components of a dental prophylaxis angle as they are being assembled into a prophylaxis angle; a movable table for carrying the mounting posts through a plurality of stations at which different assembly steps are performed;

a body station which takes an oriented body and places it on the mounting post at the body station;

a first gear member station which takes an oriented first gear member and places it in the body on the mounting post at the first near member station;

a second gear member station which takes an oriented second gear member and places it in the body on the mounting post at the second gear member station; and a tool station which attaches a tool to the second gear member on the body on the mounting post at the tool station;

wherein the mounting posts have substantially the configuration of a Doriot nose for engaging the interior of the bodies without regard to their external configuration.

2. The system according to claim 1 wherein each mounting post has a passageway therein positioned to align with a first drive shaft passage in the body, when the body is mounted on the mounting post, and a pin translatable in the passageway to selectively block the seating of a drive shaft in the first drive shaft passage in the body.

3. A system for assembling a dental prophylaxis angle from a body, first and second gear members that seat in the body, and a tool that mounts on the second gear member, the system comprising a mounting support shaped substantially like a Doriot nose for supporting the body, and having a passageway therein aligned with a passage in the body for seating the first gear member when the body is on the mounting post; and a pin translatable in the mounting post for selectively engaging a first gear member in the body and preventing the first gear member from seating in the body.

4. A system for making dental prophylaxis angles, the system comprising: a plurality of mounting posts, each adapted to support the components of a dental prophylaxis angle as the component of the prophylaxis angle are being assembled into a prophylaxis angle; a table for carrying the mounting posts past a plurality of stations at which different assembly steps are performed;

a body feeder that orients bodies from bodies loaded therein;

a body station which takes an oriented body and places it on the mounting post at the body station;

a first gear member feeder that orients first gear members from first gear members loaded therein;

a first gear member station which takes an oriented first gear member and places it in the body on the mounting post at the first gear member station;

a second gear member feeder that orients second gear members from second gear members loaded therein;

a second gear member station which takes an oriented second gear member and places it in the body on the mounting cost at the second gear member station;

a tool feeder that orients a tool from tools loaded therein;

a tool station which attaches a tool to the second gear member on the body on the mounting post at the tool station; and wherein each mounting post has substantially the configuration of a Doriot nose for engaging the interior of the bodies without regard to their external configuration.

5. The system according to claim 4 wherein each mounting post has a passageway therein positioned to align with a first gear member passage in the body when the body is mounted on the mounting post, and a pin translatable in the passageway to selectively block the seating of the first gear member in the first gear member passage in the body.

* * * * *

UNITED STATES PATENT AND TRADEMARK OFFICE
CERTIFICATE OF CORRECTION

PATENT NO. : 6,655,015 B2
DATED : December 2, 2003
INVENTOR(S) : Kraenzle

It is certified that error appears in the above-identified patent and that said Letters Patent is hereby corrected as shown below:

<u>Column 14,</u>
Line 25, replace "devises" with -- clevises --.

<u>Column 19,</u>
Line 32, replace "near" with -- gear --.

<u>Column 20,</u>
Line 31, replace "cost" with -- post --.

Signed and Sealed this

Third Day of February, 2004

JON W. DUDAS
*Acting Director of the United States Patent and Trademark Office*